United States Patent [19]
Bronstein et al.

[11] Patent Number: 6,150,136
[45] Date of Patent: *Nov. 21, 2000

[54] NUCLEOTIDE SEQUENCE ENCODING OLIGODENDROCYTE-SPECIFIC PROTEIN

[75] Inventors: Jeff M. Bronstein, Santa Monica, Calif.; Robert S. Seitz, Huntsville; Roger L. Lallone, Birmingham, both of Ala.

[73] Assignees: The Regents of the University of California, Oakland, Calif.; Research Genetics, Inc., Huntsville, Ala.

[ * ] Notice: This patent issued on a continued prosecution application filed under 37 CFR 1.53(d), and is subject to the twenty year patent term provisions of 35 U.S.C. 154(a)(2).

[21] Appl. No.: 09/084,079

[22] Filed: May 22, 1998

Related U.S. Application Data

[63] Continuation-in-part of application No. PCT/US96/18152, Nov. 13, 1996, which is a continuation-in-part of application No. 08/557,917, Nov. 14, 1995, Pat. No. 5,756,300.

[51] Int. Cl.[7] .......................... C12N 15/09; C12N 15/00; C12N 5/00; C07H 21/04
[52] U.S. Cl. ..................... 435/69.3; 435/320.1; 435/325; 536/23.5
[58] Field of Search ................................ 435/320.1, 325, 435/69.3; 536/23.5

[56] References Cited

U.S. PATENT DOCUMENTS

| | | |
|---|---|---|
| 4,396,601 | 8/1983 | Salser et al. . |
| 4,708,871 | 11/1987 | Geysen . |
| 4,923,901 | 5/1990 | Koester et al. . |
| 4,994,466 | 2/1991 | Sherman et al. . |
| 5,112,810 | 5/1992 | Nagai et al. . |
| 5,130,297 | 7/1992 | Sharma et al. . |
| 5,188,733 | 2/1993 | Wang et al. . |
| 5,194,425 | 3/1993 | Sharma et al. . |
| 5,756,300 | 5/1998 | Seitz et al. . |

FOREIGN PATENT DOCUMENTS

| | | |
|---|---|---|
| WO9215884 | 3/1992 | WIPO . |
| WO9717984 | 5/1997 | WIPO . |

OTHER PUBLICATIONS

Sevier, E.D. et al., "Monoclonal Antibodies in Clinical Immunology," *Clinical Chemistry* 27(11):1797–1805 (1981).

Xie, D. et al., "The oligodendroglial reaction to brain stab wounds: an immunohistochemical study," *Journal of Neurocytology* 24:435–448 (1995).

Schaeren–Wiemers, N. et al., "Identification of New Oligodendrocyte– and Myelin–Specific Genes by a Differential Screening Approach," *Journal Of Neurochemistry* 65(1):10–22, 1995.

Schaefer et al., "The C–DNA of COP, A novel oligodendrocyte–specific protein," *Experientia* 49:A66 (1993).

Buznikov, A. et al., "Cloning of the Human Oligodendrocyte–Specific Protein (OSP) Homologue," *Depts. Of Neurology and Pharmarcology and the Brain Research Institute*, UCLA School of Medicine, Los Angeles, CA–Abstact and Poster from Society of for Neuroscience Meeting, Nov. of 1996.

Pham—Dinh et al (Journal of Neurochemistry vol. 63 No. 6, pp. 2353–2356 Dec. 1994).

*Primary Examiner*—Albert Navarro
*Attorney, Agent, or Firm*—David A. Farah; Sheldon & Mak

[57] ABSTRACT

A protein consisting essentially of purified oligodendrocyte-specific protein or purified biologically active variants thereof, or a combination of purified oligodendrocyte-specific protein and biologically active variants thereof. A purified and isolated peptide having the sequence Ala-Lys-Tyr-Arg-Arg-Ala-Gln-Leu-Ala-Gly, residues 115–124 of SEQ ID NO:2.

9 Claims, 12 Drawing Sheets

FIG. 1A

```
1    tcgcagcagt gctcgcagcc gctctctccc catctcgagt agcccggagc cagcggctcg
61   cgagggccaa gagggcaagc ctagggaagg ctctgtccag gacgacacag ggggcacaat
121  ccgtgtgagt cgagctgcgt ggacgtcgct gcggccaccA TGGTAGCCAC TTGCCTTCAG
                                                 M  V  A   T  C  L  Q
181  GTGGTGGGTT TCGTCACGAG CTTCGTGGGT TGGATTGGCA TCATCGTCAC AACGTCCACC
      V  V  G   F  V  T    S  F  V  G  W  I  G   I  I  V    T  T  S  T
241  AATGACTGGG TGGTGACCTG CAGCTACACC ATCCCCACCT GCCGAAAAAT GGACGAACTG
      N  D  W   V  V  T    C  S  Y  T  I  P  T   C  R  K    M  D  E  L
301  GGCTCCAAGG GCCTGTGGGC TGACTGCGTC ATGGCCACTG CTGCAAACCC CTGCATCCGA
      G  S  K   G  L  W    A  D  C  V  M  A  T   C  A  N  P  H  C  I  R
361  CTGGTGGACA TCCTCATCCT TCCAGGCTAC GTGCAGGCTT GTAGAGCCCT CATGATTGCT
      L  V  D   I  L  I  L  P  G  Y   V  Q  A    C  R  A    L  M  I  A
421  GCCTCCGTTC TGGGCCTGCC CGCCATCTTG CTGCTGTTGA CAGTTCTCCC GGTGCTCCTT
      A  S  V   L  G  L  P  A  I  L   L  L  L    T  V  L    P  C  I  R
481  ATGGGCCACG AGCCTGGAGT GGCCAAGTAC AGGGGAGCCC AGCTGGCTGG GGTGCTCCTT
      M  G  H   E  P  G    V  A  K  Y  R  R  A   Q  L  A    G  V  L  L
541  ATTCTGCTGG CTCTCTGCGC CATTGTCGCC ACCATCTGGT TTCCTGTATG TGCCCACCGC
      I  L  L   A  L  C    A  I  V  A  T  I  W   F  P  V    C  A  H  R
601  GAGATCACCA TCGTGAGCTT TGGCTACTCG CTGTACGCAG GTTGGATCGG ATGCACAGTC
      E  I  T   I  V  S    F  G  Y  S  L  Y  A   G  W  I    A  T  V  M
661  TGCCTGGTGG GTGGCTGTGT CATCGTCTGC TGCTCCGGC  ATGCACAGTC ATTTGGAGAA
      C  L  V   G  G  C    V  I  V  C  C  S  G   D  A  Q    S  F  G  E
721  AACCGTTTCT ATTACTCTTC TGGTTCCAGC TCGCCAACGC ATGCCAAGAG TGCCCATGTC
      N  R  F   Y  Y  S  S  G  S  S   S  P  T    H  A  K    S  A  H  V
```

FIG. 1B

```
781   taagagggct gctccactgc ccgccgaggt gctgtaaatg ctgggcctgg gcctgggttt
841   gctcgccaca gtggggagaa gcccacttcc ctgccaggca ctaaagccaa agttctagaa
901   agtatcctgc cccggcattt tgaagtcgta acaacccacc cacccaccca ccacttcttg
961   gctgccttaa aagaaagctc tagctcagtt aatgcccaca tagtttttctc ctggagttgc
1021  gggctgtggc tgtttgctct ttcctcgggc attccattgt tgttgattaa aaaaatattt
1081  tgtttctctc ttaaattcaa atgtcttggg aacattgctg acttgggtgt ggattgggaa
1141  agaaataaaa gatgcttttc aaagggttac caagacagt ggaagccttta tagagacagc
1201  tctcttctcc ctttcggctt agtttcaagg tcacttatat ataagagata gaaatggata
1261  gattgggaac acgggtggga gggaactca gagcttccc tccacgggaa gcttctcttt
1321  tataagttga ggggttgggt gtctttttt tttttagtttg cgattttaca tttttctgta
1381  cgtacttttt caagattgat cattttata accacgggtt tcctgaaaat tctcaattca
1441  ccaatatgaa ggaaatgaac caagcagacg ttaatatgca ataaataata gtacgaagat
1501  tataacttta actgactgcc cacggtttcc aggtttgtat gctatagttt ttaatcctat
1561  ggttgcatat gcttcaaatt aacacattta aaaatctttt ctcccctct atttctgtct
1621  ccattctgtt agagaccatg aagcagtatt gtttaacata agttgtactg ttaagtttgg
1681  cttcatgggt gtaaacacca atggtctgtc agtgtctaag actctggata ctgcaagctc
1741  cgtccggtgc atttgttcag gtaaaatctg tgcaataaaa taacaaactg tcaaaaaaaa
1801  a
```

FIG. 2

```
PMP-22    4  LLLGILFLHIAVLVLLFVSTIVSQWLVGNGH............................RTDLWQN  41
OSP       6  LQVVGFVTSFVGWIG VTTSNDW VVTCSYTIPTCRKMDELGSKGLWAD              55

PMP-22   42  C..STTALGAVQHCYSSSVSEWLQSVQATMILSVIFSVLSLFLFFCQLFT              89
OSP      56  CVMATGLYHCKPLVDIL LPGYVQACRATMIAASVLGLPAILLLTVLPC              105

PMP-22   90  LTKGG..........RFYITGVFQILAGLCVMSAAAIYTVRHSEWHVNNDYS            131
OSP     106  IRMGHEPGVAKYRRAQLAGVLLILLALCAIVATIWFPV CAHREITIVS              153

PMP-22  132  YGFAYILAWVAFPLALLSGIIYVI                                       155
OSP     154  FGYSLYAGWIGAVMCLVGGCVIVC                                       177
                                    *
```

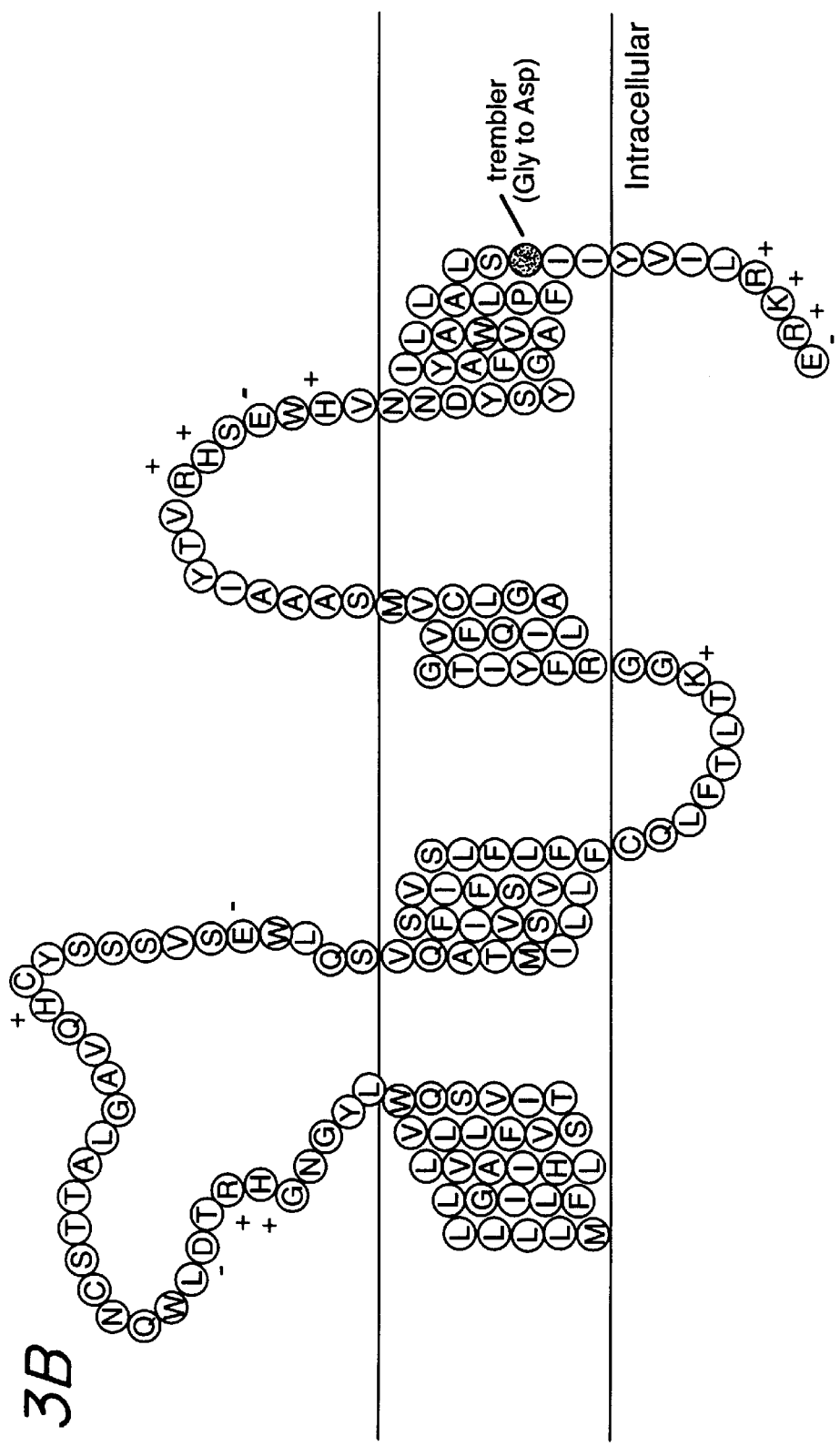
FIG. 3B  PMP-22

FIG. 5C 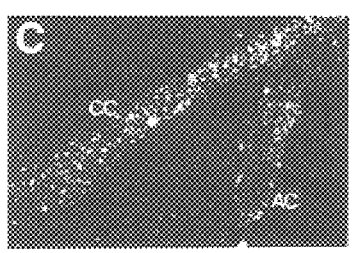 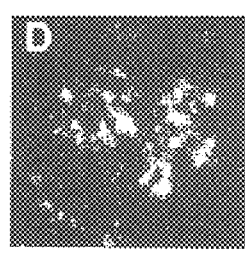 FIG. 5D
FIG. 5E 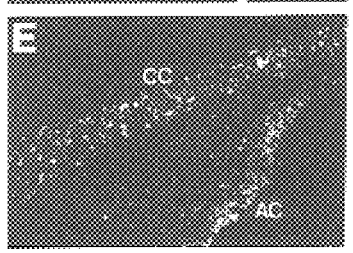 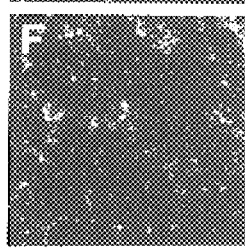 FIG. 5F

```
                             SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1801 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:1:

TCGCAGCAGT GCTCGCAGCC GCTCTCTCCC CATCTCGAGT AGCCCGGAGC CAGCGGCTCG      60

CGAGGGCCAA GAGGGCAAGC CTAGGGAAGG CTCTGTCCAG GACGACACAG GGGGCACAAT     120

CCGTGTGAGT CGAGCTGCGT GGACGTCGCT GCGGCCACC ATG GTA GCC ACT TGC       174
                                           Met Val Ala Thr Cys
                                             1               5
```

-continued

| | | |
|---|---|---|
| CTT CAG GTG GTG GGT TTC GTC ACG AGC TTC GTG GGT TGG ATT GGC ATC<br>Leu Gln Val Val Gly Phe Val Thr Ser Phe Val Gly Trp Ile Gly Val<br>10                    15                20 | | 222 |
| ATC GTC ACA ACG TCC ACC AAT GAC TGG GTG GTG ACC TGC AGC TAC ACC<br>Ile Val Thr Thr Ser Thr Asn Asp Trp Val Val Thr Cys Ser Tyr Thr<br>          25                    30                  35 | | 270 |
| ATC CCC ACC TGC CGA AAA ATG GAC GAA CTG GGC TCC AAG GGC CTG TGG<br>Ile Pro Thr Cys Arg Lys Leu Asp Glu Leu Gly Ser Lys Gly Leu Trp<br>          40                    45                50 | | 318 |
| GCT GAC TGC GTC ATG GCC ACT GGT CTC TAC CAC TGC AAA CCC CTG GTG<br>Ala Asp Cys Val Met Ala Thr Gly Leu Tyr His Cys Lys Pro Leu Val<br>55                      60                65 | | 366 |
| GAC ATC CTC ATC CTT CCA GGC TAC GTG CAG GCT TGT AGA GCC CTC ATG<br>Asp Ile Leu Ile Leu Pro Gly Tyr Val Gln Ala Cys Arg Ala Leu Met<br>70                      75                80                85 | | 414 |
| ATT GCT GCC TCC GTT CTG GGC CTG CCC GCC ATC TTG CTG CTG TTG ACA<br>Ile Ala Ala Ser Val Leu Gly Leu Pro Ala Ile Leu Leu Leu Leu Thr<br>          90                    95                100 | | 462 |
| GTT CTC CCC TGC ATC CGA ATG GGC CAC GAG CCT GGA GTG GCC AAG TAC<br>Val Leu Pro Cys Ile Arg Met Gly His Glu Pro Gly Val Ala Lys Tyr<br>          105                110              115 | | 510 |
| AGG CGA GCC CAG CTG GCT GGG GTG CTC CTT ATT CTG CTG GCT CTC TGC<br>Arg Arg Ala Gln Leu Ala Gly Val Leu Leu Ile Leu Leu Ala Leu Cys<br>120                     125               130 | | 558 |
| GCC ATT GTC GCC ACC ATC TGG TTT CCT GTA TGT GCC CAC CGC GAG ATC<br>Ala Ile Val Ala Thr Ile Trp Phe Pro Val Cys Ala His Arg Glu Thr<br>135                     140               145 | | 606 |
| ACC ATC GTG AGC TTT GGC TAC TCG CTG TAC GCA GGT TGG ATC GGT GCT<br>Thr Ile Val Ser Phe Gly Tyr Ser Leu Tyr Ala Gly Trp Ile Gly Ala<br>150                   155               160               165 | | 654 |
| GTG ATG TGC CTG GTG GGT GGC TGT GTC ATC GTC TGC TGC TCC GGG GAT<br>Val Leu Cys Leu Val Gly Gly Cys Val Ile Val Cys Cys  Gly Asp<br>          170                    175               180 | | 702 |
| GCA CAG TCA TTT GGA GAA AAC CGT TTC TAT TAC TCT TCT GGT TCC AGC<br>Ala Gln Ser Phe Gly Glu Asn Arg Phe Tyr Tyr Ser Ser Gly Ser Ser<br>          185                190              195 | | 750 |
| TCG CCA ACG CAT GCC AAG AGT GCC CAT GTC TAAGAGGGCT GCTCCACTGC<br>Ser Pro Thr His Ala Lys Ser Ala His Val<br>200                     205 | | 800 |
| CCGCCGAGGT GCTGTAAATG CTGGGCCTGG GCCTGGGTTT GCTCGCCACA GTGGGAGAA | | 860 |
| GCCCACTTCC CTGCCAGGCA CTAAAGCCAA AGTTCTAGAA AGTATCCTGC CCCGGCATTT | | 920 |
| TGAAGTCGTA ACAACCCACC CACCCACCCA CCACTTCTTG GCTGCCTTAA AGAAAGCTC | | 980 |
| TAGCTCAGTT AATGCCCACA TAGTTTTCTC CTGGAGTTGC GGGCTGTGGC TGTTTGCTCT | | 1040 |
| TTCCTCGGGC ATTCCATTGT TGTTGATTAA AAAAATATTT TGTTTCTCTC TTAAATTCAA | | 1100 |
| ATGTCTTGGG AACATTGCTG ACTTGGGTGT GGATTGGGAA AGAAATAAAA GATGCTTTTC | | 1160 |
| AAAGGGTTAC CAACGACAGT GGAAGCCTTA TAGAGACAGC TCTCTTCTCC CTTTCGGCTT | | 1220 |
| AGTTTCAAGG TCACTTATAT ATAAGAGATA GAAATGGATA GATTGGGAAC ACGGGTGGGA | | 1280 |
| GGGGAACTCA GAGCTTTCCC TCCACGGGAA GCTTCTCTTT TATAAGTTGA GGGGTTGGGT | | 1340 |
| GTCTTTTTTT TTTTAGTTTG CGATTTTACA TTTTTCTGTA CGTACTTTTT CAAGATTGAT | | 1400 |
| CATTTTTATA ACCACGGGTT TCCTGAAAAT TCTCAATTCA CCAATATGAA GGAAATGAAC | | 1460 |
| CAAGCAGACG TTAATATGCA ATAAATAATA GTACGAAGAT TATAACTTTA ACTGACTGCC | | 1520 |
| CACGGTTTCC AGGTTTGTAT GCTATAGTTT TTAATCCTAT GGTTGCATAT GCTTCAAATT | | 1580 |
| AACACATTTA AAAATCTTTT CTCCCCTTCT ATTTCTGTCT CCATTCTGTT AGAGACCATG | | 1640 |

```
AAGCAGTATT GTTTAACATA AGTTGTACTG TTAAGTTTGG CTTCATGGGT GTAAACACCA      1700

ATGGTCTGTC AGTGTCTAAG ACTCTGGATA CTGCAAGCTC CGTCCGGTGC ATTTGTTCAG      1760

GTAAAATCTG TGCAATAAAA TAACAAACTG TCAAAAAAAA A                         1801

(2) INFORMATION FOR SEQ ID NO:2:

(i) SEQUENCE CHARACTERISTICS:
        (A) LENGTH: 207 amino acid residues
        (B) TYPE: amino acid
        (D) TOPOLOGY: linear (ii) MOLECULE TYPE: protein (xi) SEQUENCE DESCRIPTION: SEQ ID NO:2:

Met Val Ala Thr Cys Leu Gln Val Val Gly Phe Val Thr Ser Phe Val Gly Trp
 1               5                  10                  15

Ile Gly Ile Ile Val Thr Thr Ser Thr Asn Asp Trp Val Val Thr Cys Ser Tyr
        20                  25                  30                  35

Thr Ile Pro Thr Cys Arg Lys Met Asp Glu Leu Gly Ser Lys Gly Leu Trp Ala
                40                  45                  50

Asp Cys Val Met Ala Thr Gly Leu Tyr His Cys Lys Pro Leu Val Asp Ile Leu
55                  60                  65                  70

Ile Leu Pro Gly Tyr Val Gln Ala Cys Arg Ala Leu Met Ile Ala Ala Ser Val
            75                  80                  85                  90

Leu Gly Leu Pro Ala Ile Leu Leu Leu Thr Val Leu Pro Cys Ile Arg Met
                    95                  100                 105

Gly His Glu Pro Gly Val Ala Lys Tyr Arg Arg Ala Gln Leu Ala Gly Val Leu
    110                 115                 120                 125

Leu Ile Leu Leu Ala Leu Cys Ala Ile Val Ala Thr Ile Trp Phe Pro Val Cys
        130                 135                 140

Ala His Arg Glu Ile Thr Ile Val Ser Phe Gly Tyr Ser Leu Tyr Ala Gly Trp
145                 150                 155                 160

Ile Gly Ala Val Met Cys Leu Val Gly Gly Cys Val Ile Val Cys Cys Ser Gly
        165                 170                 175                 180

Asp Ala Gln Ser Phe Gly Glu Asn Arg Phe Tyr Tyr Ser Ser Gly Ser Ser Ser
                185                 190                 195

Pro Thr His Ala Lys Ser Ala His Val
    200                 205

(2) INFORMATION FOR SEQ ID NO:3:

(i) SEQUENCE CHARACTERISTICS:
        (A) LENGTH: 161 amino acid residues
        (B) TYPE: amino acids
        (D) TOPOLOGY: linear (ii) MOLECULE TYPE: protein (xi) SEQUENCE DESCRIPTION: SEQ ID NO:3:

Met Leu Leu Leu Leu Gly Ile Leu Phe Leu His Ile Ala Val Leu Val Leu
 1               5                  10                  15

Leu Phe Val Ser Thr Ile Val Ser Gln Trp Leu Val Gly Asn Gly His Thr Thr
        20                  25                  30                  35

Asp Leu Trp Gln Asn Cys Thr Thr Ser Ala Leu Gly Ala Val Gln His Cys Tyr
                40                  45                  50

Ser Ser Ser Val Ser Glu Trp Leu Gln Ser Val Gln Ala Thr Met Ile Leu Ser
55                  60                  65                  70
```

```
Val Ile Phe Ser Val Leu Ala Leu Phe Leu Phe Cys Gln Leu Phe Thr Leu
        75                  80                  85                  90

Thr Lys Gly Gly Arg Phe Tyr Ile Thr Gly Phe Phe Gln Ile Leu Ala Gly Leu
                95                  100                 105

Cys Val Met Ser Ala Ala Ile Tyr Thr Val Arg His Ser Glu Trp His Val
        110                 115                 120                 125

Asn Thr Asp Tyr Ser Tyr Gly Phe Ala Tyr Ile Leu Ala Trp Val Ala Phe Pro
                130                 135                 140

Leu Ala Leu Leu Ser Gly Ile Ile Tyr Val Ile Leu Arg Lys Arg Glu Leu
145                 150                 155                 160
```

(2) INFORMATION FOR SEQ ID NO:4:

(i) SEQUENCE CHARACTERISTICS:
        (A) LENGTH: 2243 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:4:

```
GTCGACCCTG GCGGCCACC ATG GTG GCC ACG TGC CTG CAG GTG GTG GGC TTC         52
                    Met Val Ala Thr Cys Leu Gln Val Val Gly Phe
                      1               5                  10

GTC ACG AGC TTC GTG GGC TGG ATC GGG GTC ATC GTG ACC ACC TCC ACC         100
Val Thr Ser Phe Val Gly Trp Ile Gly Val Ile Val Thr Thr Ser Thr
            15                  20                  25

AAT GAC TGG GTG GTG ACC TGC GGC TAC ACC ATC CCC ACC TGC CGC AAG         148
Asn Asp Trp Val Val Thr Cys Gly Tyr Thr Ile Pro Thr Cys Arg Lys
        30                  35                  40

CTG GAT GAG CTG GGC TCC AAG GGG CTG TGG GCC GAC TGC GTC ATG GCC         196
Leu Asp Glu Leu Gly Ser Lys Gly Leu Trp Ala Asp Cys Val Met Ala
    45                  50                  55

ACG GGG CTG TAC CAC TGC AAG CCC CTG GTG GAC ATC CTC ATC CTG CCG         244
Thr Gly Leu Tyr His Cys Lys Pro Leu Val Asp Ile Leu Ile Leu Pro
60                  65                  70                  75

GGC TAC GTG CAG GCC TGC CGC GCC CTG ATG ATT GCT GCC TCG GTC CTG         292
Gly Tyr Val Gln Ala Cys Arg Ala Leu Met Ile Ala Ala Ser Val Leu
                80                  85                  90

GGT CTG CCG GCC ATT TTA CTG CTG CTG ACT GTT CTT CCC TGC ATC CGG         340
Gly Leu Pro Ala Ile Leu Leu Leu Leu Thr Val Leu Pro Cys Ile Arg
            95                  100                 105

ATG GGC CAG GAG CCC GGT GTG GCT AAG TAC AGG CGG GCC CAG CTG GCT         388
Met Gly Gln Glu Pro Gly Val Ala Lys Tyr Arg Arg Ala Gln Leu Ala
        110                 115                 120

GGT GTT TTG CTC ATT CTG CTG GCT CTC TGC GCC CTT GTT GCC ACC ATC         436
Gly Val Leu Leu Ile Leu Leu Ala Leu Cys Ala Leu Val Ala Thr Ile
    125                 130                 135

TGG TTC CCT GTG TGC GCC CAC CGT GAG ACC ACC ATC GTG AGC TTT GGC         484
Trp Phe Pro Val Cys Ala His Arg Glu Thr Thr Ile Val Ser Phe Gly
140                 145                 150                 155

TAC TCC CTG TAT GCA GGC TGG ATT GGT GCT GTG CTG TGC CTC GTG GGT         532
Tyr Ser Leu Tyr Ala Gly Trp Ile Gly Ala Val Leu Cys Leu Val Gly
                160                 165                 170

GGC TGT GTC ATC CTC TGC TGC GCT GGA GAT GCC CAG GCC TTT GGT GAA         580
Gly Cys Val Ile Leu Cys Cys Ala Gly Asp Ala Gln Ala Phe Gly Glu
            175                 180                 185

AAC GTT TCT ACT ACA CTG CGG GCT CTA GCT CCC CGA CTC ATG CGA AGA         628
Asn Val Ser Thr Thr Leu Arg Ala Leu Ala Pro Arg Leu Met Arg Arg
        190                 195                 200
```

```
GTG CCC ACG TAT AAG AGG GCT GCC CGG CTG CCC ACA GAG GTG CTG        673
Val Pro Thr Tyr Lys Arg Ala Ala Arg Leu Pro Thr Glu Val Leu
    205                 210                 215

TAGATGCTGG GCCCAGGGCC CTAGGTTTGC TCGTCACAGT GTGGGGAAGC CCATTCCTCT  733

GCCAGGCTCT AAAGCCAAAG GTCTAGAAAA GCATCCAGCC TGGGCAACAA GAGCAAAAAA  793

CTCTGTCTCA AATAATAATA ATGATAATAG TAATATTTCT AATTACTAGC CTAGTATAGA  853

CACTACTGGG GACCAGGCTA CTCCTGTTCG TTGCCTGTAG ATGTTTATTA TTTTAGCTGG  913

ATGGTATAAG TTTGATGATG GACTGTTCAT ATGTTCTTGC AAATGCAGTG AACTATATTA  973

CACACCATTA ATTATAAGTC TTCCACACTC AGATTCTGTG AAAGTCCCCC TAATTTGTTG 1033

ATGACATAAA GCTCCACCTC TACAATCATA TGCCTTTTTT AAGGAGTGTC ATGAATCCAG 1093

ATACTGAGAT CAGGAACTTA CATAAGGCCA ACTAAAAAAA CCCTTTACAA TGTATTTTAC 1153

ATATATTATA GTTTGTAAGT ATAAACATTC AACTACTGTT AATGGACTTC TAAGAGAAGT 1213

CGAGTCATTT CTGTGTGTTG GAACCTCCTG TGATCATCAT CCAGAGGAAG TTTCATATAC 1273

GCTGGAAATC CAGTTTCATA AAATGTTACC TAAAATGTAA TGACCTCAAA TGGAGTGTAC 1333

TCAGTAACTC TAGAATAGGA AGGATCTTCT GATCTTTGCA AGATTGCAG AGGCGTCTCT 1393

GATGAGATAA TTGAGTTCCT TCCTCTGATT TTCTGAATTG AACCTGCAGC AATTCATCTT 1453

TTTAATCAAG CTGCTAAAGT ACAATGGATC TCTGCAGTGA TTTAGGATGT CCAGTTCTAG 1513

GAAGCATTGT TCTGGGCTTT CAGAATGTAG GAGGAGATCT TTGTACTATT TCAGTCTTTT 1573

TGATAAACAA GTCATAAAGA AGAAACCAGT TGTCTGAGAT TGCCATAAAC TGTAAACTCT 1633

TTGACAGTAA CATAAAGAGA TGGATTAAAT TGGAATACAA CCAAATTTAT CTGGAGGTTC 1693

TGAACAAAGG CTGGTCACTG AAGTAATCAT AGAATTGACA GCCAAGCACT CCTTTCCATC 1753

AGTTAAGTAA AGAACGAAAT AAACTGTTTA CATGATTTTA TCCCCATTC TGAATGGAAG 1813

ACAAAAGCTT CAGGAACCCT TGATGGCAGA TAAAATGTCC TGTGGAGTCT TCTTGGTAAT 1873

CATTAGAGCA CGTTGTTTTA TCATCTGAGA CAGTAAGAAC CGAAACAATT TAACAATGTC 1933

TTCAAAGGCT TTGCTAGATT AGACAGTACG AAAAATAAAC ATCAAGAATG TGGAAACTAT 1993

CATGTACAAG AAAGACCATG CAATGTTGAC TCTTTTTTTT ATTTTTTCCT CTCTCTCTTT 2053

TGAGACAGAG TCTTGCTCTG AGTCCAGTGG CGCGGTCTCT GCTCACTGCA ACCTCTGCCT 2113

CCCGGGTTGA AGCAATTCTC CTGCCTAGAC CTCCTGGGTG GCTGGGGTTC CAGGGGCCCG 2173

CCACTATGCC TGGCTGCTTT TTGTATTTTT AGTGGAGACG GGGTTTCGCC ATGTTGGCCA 2233

GGCTGCTCTC                                                      2243

(2) INFORMATION FOR SEQ ID NO:5:

(i) SEQUENCE CHARACTERISTICS:
        (A) LENGTH: 218 amino acid residues
        (B) TYPE: amino acid
        (D) TOPOLOGY: linear (ii) MOLECULE TYPE: protein (xi) SEQUENCE DESCRIPTION: SEQ ID NO:5:

Met Val Ala Thr Cys Leu Gln Val Val Gly Phe Val Thr Ser Phe Val Gly Trp
                5                   10                  15

Ile Gly Val Ile Val Thr Thr Ser Thr Asn Asp Trp Val Val Thr Cys Gly Tyr
        20                  25                  30                  35

Thr Ile Pro Thr Cys Arg Lys Leu Asp Glu Leu Gly Ser Lys Gly Leu Trp Ala
            40                  45                  50
```

-continued

```
Asp Cys Val Met Ala Thr Gly Leu Tyr His Cys Lys Pro Leu Val Asp Ile Leu
 55              50                   65              70

Ile Leu Pro Gly Tyr Val Gln Ala Cys Arg Ala Leu Met Ile Ala Ala Ser Val
         75              80              85                       90

Leu Gly Leu Pro Ala Ile Leu Leu Leu Thr Val Leu Pro Cys Ile Arg Met
             95             100             105

Gly Gln Glu Pro Gly Val Ala Lys Tyr Arg Arg Ala Gln Leu Ala Gly Val Leu
        110             115             120             125

Leu Ile Leu Leu Ala Leu Cys Ala Leu Val Ala Thr Ile Trp Phe Pro Val Cys
            130             135             140

Ala His Arg Glu Thr Thr Ile Val Ser Phe Gly Tyr Ser Leu Tyr Ala Gly Trp
145             150             155             160

Ile Gly Ala Val Leu Cys Leu Val Gly Gly Cys Val Ile Leu Cys Cys Ala Gly
        165             170             175             180

Asp Ala Gln Ala Phe Gly Glu Asn Val Ser Thr Thr Leu Arg Ala Leu Ala Pro
            185             190             195

Arg Leu Met Arg Arg Val Pro Thr Tyr Lys Arg Ala Ala Arg Leu Pro Thr Glu
        200             205             210             215

Val Leu
```

NUCLEOTIDE SEQUENCE ENCODING OLIGODENDROCYTE-SPECIFIC PROTEIN

CROSS-REFERENCE TO RELATED APPLICATIONS

The present application is a continuation-in-part of PCT application PCT/US96/18152, entitled OLIGODENDROCYTE-SPECIFIC PROTEIN AND METHOD FOR TREATING DISEASE, filed Nov. 13, 1996, and is a continutation-in-part of U.S. patent application Ser. No. 08/557,917, entitled OLIGODENDROCYTE-SPECIFIC PROTEIN AND METHOD FOR DIAGNOSING AND TREATING DISEASE, filed Nov. 14, 1995, now U.S. Pat. No. 5,756,300; both incorporated herein by reference in their entirety.

STATEMENT REGARDING FEDERALLY SPONSORED RESEARCH OR DEVELOPMENT

This invention was made with Government support under Grant No. NS01596, awarded by the National Institutes of Health. The Government has certain rights in this invention.

NOTICE OF INCLUSION OF COPYRIGHTED MATERIAL

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND

Myelin is a substance composed of a group of myelin-specific proteins which form a complex multilamellar sheath surrounding neuronal axons. Myelin plays a critical role in the normal functioning of the nervous system. Myelin forms early in development and its formation involves the activation of a group of unique genes. Some of these genes appear to also regulate the proliferation, migration and differentiation of Schwann cells in the peripheral nervous system, in addition to the formation of the myelin sheath.

Eighty to ninety percent of total myelin protein in the central nervous system corresponds to myelin basic proteins (MBPs) and proteolipid proteins (PLP and DM20). Myelin in the peripheral nervous system (PNS) is mainly composed of protein zero ($P_O$) and peripheral myelin protein 22 (PMP-22), as well as myelin basic proteins.

The function of myelin proteins is not entirely known. However, animals carrying specific gene mutations which encode for defective myelin proteins provide some information. For example, the MBP gene which normally encodes for a family of at least six closely related membrane proteins (14–21.5 kDa) generated by RNA splicing events is substantially missing in the shiverer mouse (shi). This defect results in the considerably reduced formation of myelin and abnormally compacted myelin sheaths in the central nervous system. However, the defect causes minimal changes in the peripheral nervous system of shi mice, suggesting that other proteins serve the functions of MBPs in the peripheral nervous system. By comparison, defects in the gene encoding $P_O$ are known which cause hypomyelination and abnormal compaction in the peripheral nervous system.

Further, defects in the gene encoding PLP result in the jimpy mouse phenotype and human Pelizaeus-Merzbacher disease. Both diseases result in the death of oligodendrocytes and in the formation of abnormal membrane apposition in the central nervous system.

By comparison, alterations in the PMP-22 gene cause the trembler (tr) mouse phenotype, as well as the human disease Charcot-Marie-Tooth IA and hereditary neuropathy with liability to pressure palsy. In addition to being a structural myelin protein, PMP-22 appears to regulate Schwann cell proliferation since it is identical to the growth arrest-specific gene gas-3. Further, the over expression of PMP-22 inhibits growth rates in Schwann cells while the under expression of PMP-22 increases Schwann cell division rate. The central nervous system homologue to PMP-22 is currently unknown.

Besides the disorders of myelin described above, there exist many other disorders of myelin for which etiologies are not yet known. These disorders include leukodystrophies and multiple sclerosis (MS).

Multiple sclerosis is characterized by recurrent attacks of focal or multi-focal neurologic dysfunction. In addition, there exists a chronic progressive form. Neurologic dysfunction stems from discrete demyelinating lesions in the central nervous system. While multiple sclerosis can affect any age group, its onset is most commonly in early adult life. Attacks can occur frequently or infrequently. Further, the neurologic dysfunction associated with attacks can ameliorate completely or can leave a residual permanent neurologic deficit.

Multiple sclerosis is currently diagnosed on the basis of history, and on the demonstration of lesions in the central nervous system by a variety of laboratory tests including magnetic resonance imaging scans. However, a diagnosis of multiple sclerosis is frequently difficult to make because of its varied presentation.

Evidence has suggested that multiple sclerosis is an autoimmune disorder. That evidence includes studies which show that the immunization of animals with myelin proteins, as well as the adoptive transfer of activated CD4 cells specific for some myelin proteins, result in a demyelinating disease similar to multiple sclerosis. Further, acute lesions in multiple sclerosis demonstrate macrophages, T cells and deposits of immunoglobulin.

Besides multiple sclerosis, there are many autoimmune diseases which cause significant morbidity and mortality in human and animal populations. Among the human diseases believed to be autoimmune in origin are some forms of arthritis, diabetes, Grave's disease, Hashimoto's, myasthenia gravis, scleroderma and systemic lupus erythematous. Diagnosis of the various autoimmune diseases is made on the basis of history, physical exam and laboratory tests, but the diagnoses can also be difficult and imprecise.

Further, the use of synthetic peptides as antigens in the diagnosis and therapy of autoimmune and other diseases and conditions is currently the subject of considerable study. Progress in the use of synthetic peptides has been hampered, however, because of the difficulty in identifying regions of peptides which serve as epitopes. Commonly, epitopes are predicted on the bases of calculations of hydrophobic and hydrophilic amino acid content to determine which amino acids will be expressed on the cell surface. This approach has met with only limited success.

Therefore, it would be advantageous to know the central nervous homologue to PMP-22. Further, it would be advantageous to have an additional method for diagnosing or for confirming the diagnosis of multiple sclerosis. Still further, it would be advantageous to have a method for diagnosing or for confirming the diagnosis of various other autoimmune diseases. Also, it would be advantageous to have a device and method for identifying regions of peptides, proteins or protein homologues which serve as epitopes.

FIGURES

These and other features, aspects, and advantages of the present invention will become better understood with regard to the following description, appended claims, and accompanying figures where:

FIGS. 1A–1B illustrate a mammalian (mouse) oligodendrocyte-specific protein cDNA sequence, SEQ ID NO:1, with the deduced amino acid sequence, SEQ ID NO:2, shown below the cDNA sequence;

FIG. 2 compares mouse PMP-22 amino acid sequence, SEQ ID NO:3, and oligodendrocyte-specific protein amino acid sequence, SEQ ID NO:2;

FIGS. 3A–3B illustrate the predicted structure of mouse oligodendrocyte-specific protein, SEQ ID NO:2, and PMP-22, SEQ ID NO:3;

FIGS. 5A–5F illustrate cellular localization of oligodendrocyte-specific protein mRNA;

SUMMARY

Figure 3A:
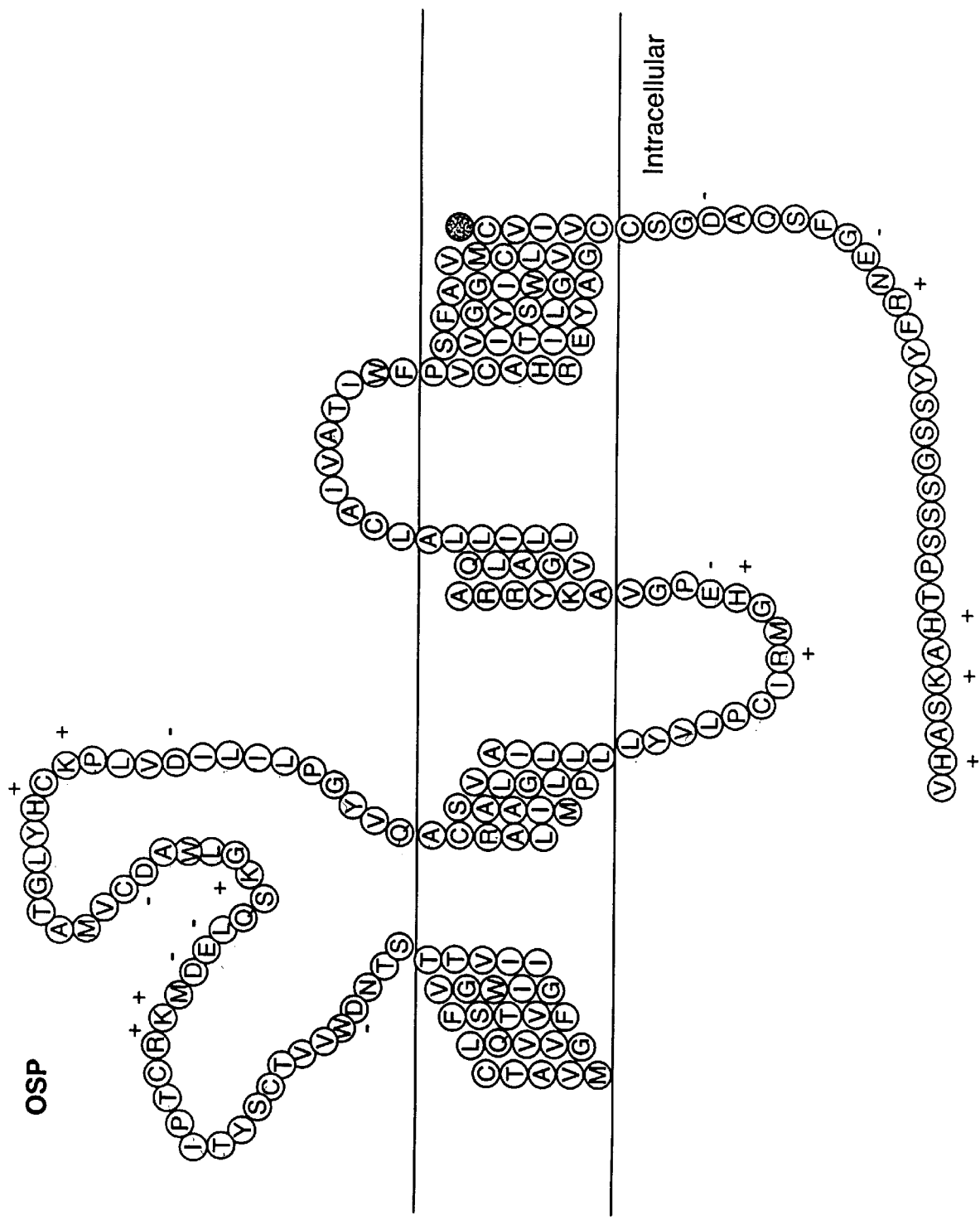

According to one aspect of the present invention, there is provided a protein consisting essentially of purified human oligodendrocyte-specific protein or purified biologically active variants thereof, or a combination of purified oligodendrocyte-specific protein and biologically active variants thereof. The protein can be recombinant and can have an amino acid sequence substantially as set forth in ID SEQ NO:5. According to another embodiment of the present invention, there is provided a protein recognized by a monoclonal antibody having affinity to a protein according to the present invention.

Further, there is provided a DNA sequence encoding for human OSP, or its complementary strands; and a DNA sequence which hybridizes to any of these sequences and which codes on expression for a protein having biological activity of oligodendrocyte-specific protein, or its complementary strands.

According to another embodiment of the present invention, there is provided a high affinity monoclonal antibody which immunoreacts with human oligodendrocyte-specific protein. The antibody can have an Fc portion selected from the group consisting of the IgM class, the IgG class and the IgA class, or can have another Fc portion.

According to still another embodiment of the present invention, there is provided a method of diagnosing a disease, such as meningioma, comprising the steps of, first determining the amount of OSP present in a biological sample. Then, the determined amount is compared to a known amount for a normal sample or a sample from a known disease. The sample can be selected from the group consisting of cerebral spinal fluid, blood, tears, saliva and a biopsy specimen.

According to another embodiment of the present invention, there is provided a method of making a monoclonal antibody which immunoreacts with oligodendrocyte-specific protein comprising the steps of, first, administering to a host oligodendrocyte-specific protein in an amount sufficient to induce the production of antibodies to the oligodendrocyte-specific protein from the antibody-producing cells. Then, the antibody-producing cells are recovered from the host. Next, the cell hybrids are formed by fusing the antibody-producing cell to cells capable of substantially unlimited reproduction. The hybrids are cultured and the monoclonal antibodies are collected as a product of the hybrids. In a preferred embodiment, the cells capable of substantially unlimited reproduction are myeloma cells.

According to another embodiment of the present invention, there is provided a vector containing a DNA molecule encoding oligodendrocyte-specific protein or encoding its complimentary strand. There is further provided a prokaryotic or eukaryotic host cell stably transformed or transfected by the vector.

According to another embodiment of the present invention, there is provided a method of making a protein according to the present invention, comprising the steps of, first, culturing a microorganism transformed with DNA encoding for oligodendrocyte-specific protein. Then, the oligodendrocyte-specific protein or its complementary strands is recovered.

According to another embodiment of the present invention, there is provided a recombinant oligodendrocyte-specific protein. There is also provided a purified and isolated peptide having the sequence Ala-Lys-Tyr-Arg-Arg-Ala-Gln-Leu-Ala-Gly, residues 115–124 of SEQ ID NO:2. This peptide can be recombinant. There is also provided a peptide recognized by a monoclonal antibody having affinity to this peptide. There is further provided a high affinity monoclonal antibody which immunoreacts with this peptide. The antibody can have an Fc portion selected from the group consisting of the IgM class, the IgG class and the IgA class, or can have another Fc portion.

DESCRIPTION

According to one aspect of the present invention, there is provided a 22 kDa protein referred to herein as "oligodendrocyte-specific protein," and a cDNA encoding oligodendrocyte-specific protein. The amino acid sequence and predicted protein structure of oligodendrocyte-specific protein share similarities with peripheral myelin protein-22 (PMP-22). Further, oligodendrocyte-specific protein appears to be predominantly expressed in myelinating cells of the central nervous system and, like PMP-22, appears to be associated with the control of cellular growth of myelinating cells. Therefore, oligodendrocyte-specific protein is a likely candidate for the central nervous system homologue to PMP-22.

Referring now to FIG. 1, there is illustrated a full-length cDNA sequence of a mammalian (mouse) oligodendrocyte-specific protein, SEQ ID NO:1, with the deduced amino acid sequence, SEQ ID NO:2, shown below the open reading frame nucleic acid sequence. The initiation and the termination codons are underlined and the polyadenylation signal is double underlined. The GenBank accession number for the oligodendrocyte-specific protein cDNA sequence, SEQ ID NO:1, shown in FIG. 1 is U19582.

I. DETERMINATION OF MURINE OLIGODENDROCYTE-SPECIFIC PROTEIN cDNA (a) Construction Of cDNA Libraries:

In order to construct the appropriate cDNA library, total RNA was isolated from the cervical region of the complete cervical spinal cord region of 30 to 40 day old NFR mice (originally described from Michael FW Festing, MRC Toxicology Unit, Hodgkin Building, University of Leicester, UK, obtained from the NIH, Bethesda, Md.) using the guanidine thiocyanate/CsCl procedure (Chirgwin, J. M., Przybyla, A. E., McDonald, R. J., and Rutter, W. J. "Isolation of Biologically Active Ribonucleic Acid From Sources Enriched in Ribonuclease," Biochemistry 18:5294–9 (1979), incorporated herein by reference in its entirety), which was then subdivided into dorsal and ventral cord components. Next, messenger RNA was isolated from a 100 mg sample of the isolated total RNA using oligo-dT resin (Pharmacia Biotech Inc., Piscataway, N.J.). Double-stranded cDNA with cohesive EcoRI ends was synthesized from 3 µg of mRNA using a cDNA synthesis kit (Pharmacia). Then, the cDNAs were ligated into λ Zap II phagemid vector (Stratagene® Cloning Systems, La Jolla, Calif.) to prepare a complete spinal cord library and the cDNAs were ligated into pT7T3 plasmid vector (Pharmacia, Piscataway, N.J.) to prepare a dorsal cord library.

The cDNA/phagemid ligation mixture was packaged with Gigapack packing extract and transformed into *Escherichia coli* XL-1 Blue cells (Stratagene). The titer was estimated to be $3 \times 10^6$ plaque-forming units (pfu). The dorsal cord cDNA/pT7T3 ligate was electroporated into J5 electrocompetent cells (BioRad Laboratories, Inc., Hercules, Calif.) using a BioRad Gene Pulser® Apparatus. The resulting dorsal-cord library was estimated to contain $6 \times 10^7$ tranformants.

(b) Subtractive Probe Preparation and Screening:

The dorsal-cord plasmid library was amplified. Next, the plasmid DNA was isolated, digested with EcoRI, and biotinylated at approximately every 250 base pairs using photo-activated biotin with long-arm spacers (Vector Laboratories, Inc., Burlingame, Calif.) to reduce steric hindrance. Single-stranded [$^{32}$P]cDNA probe was prepared from 50 µg total RNA isolated from complete spinal cords of 30 to 40 day-old mice using oligo(dT) (Gibco BRL Life Technologies™, Gaithersberg, Md.) as a primer as described by Krug and Berger (Krug, M. S. and Berger, S. L., "Method of Enzymology". Berger, S. L. and Kimmel, A. R. (Eds), *San Diego Acad Press*, 152:316–324 (1987), incorporated herein by reference in its entirety).

Approximately 190 µg of biotinylated-dorsal cord cDNA was mixed with 2.0 µg of spinal cord first-strand [$^{32}$P]-cDNA. The mixture was denatured and hybridized using the phenol emulsion reassociation technique (Kohne, D. E., Levison, S. A., and Byers, M. J., "Room Temperature Method for Increasing the Rate of DNA Reassociation by Many Thousand Fold: The Phenol Emulsion Reassociation Technique," *Biochemistry* 16:5329–5341 (1977); Travis, G. H., and Sutcliff, J. G., "Phenol Emulsion-Enhanced DNA-Driven Subtractive cDNA Cloning: Isolation of Low-Abundance Monkey Cortex-Specific mRNAs," *Proc.Natl.Acad.Sci. U.S.A.* 85:1696–1700 (1988); Bowes, C., Danciger, M., Kozak, C. A., and Farber, D. B., "Isolation of a Candidate cDNA for the Gene Causing Retinal Degeneration in the Mouse," *Proc.Natl.Acad.Sci. U.S.A.* 89:9722–9726 (1989), each incorporated herein by reference in its entirety). After 48 hrs of hybridization, the phenol was removed by $CHCL_3$ extraction and ethanol precipitation. The single-stranded ventral-cord enriched [$^{32}$P]cDNA was separated from biotin-DNA and biotin-DNA-[$^{32}$P]-DNA duplexes by passage over a streptavidin-sepharose column (Pharmacia).

Approximately $1 \times 10^6$ pfu of the complete spinal cord phagemid library were plated and duplicate "plaque lifts" were prepared by the method of Benton and Davis (Benton, W. D. and Davis, R. W., "Screening of Igt Recombinant Cloning by Hybridization to Single Plaques In Situ," *Science* 196:180–183 (1987), incorporated herein by reference in its entirety) using nylon Hybond N+ filters (Amersham Life Sciences, Inc., Arlington Heights, Ill.). A first set of filters was hybridized with the [$^{32}$P]-ventral cord-enriched subtractive probe and a second set of filters was hybridized with single-stranded [$^{32}$P]-cDNAs made from dorsal spinal cord total RNA, both for 48 hrs at 65° C. After hybridization, the filters were washed in 0.2×SSC (1×SSC=0.15 M NaCl, 0.015 NaCitrate, pH 7.0) plus 0.1% $NaDodSO_4$ (SDS) at 61° C., and then exposed to X-ray film for autoradiography. Clones which hybridized to the subtracted probe and which showed limited hybridization to dorsal cord single-stranded [$^{32}$P]-cDNAs were isolated and rescreened at low plaque density using duplicate lifts and [$^{32}$P]-cDNA probes made from dorsal and ventral spinal cord RNA.

In vivo excision and rescue of double-stranded recombinant pBluescript SK(-) plasmids out of the λ ZAP II phagemids was performed on the ventral-cord enriched phage plaques as described by the protocol provided by Stratagene, manufacturer of the pBluescript SK(-). Plasmid DNA was isolated using Magic Mini Preps (Promega, Corporation, Madison, Wis.).

(c) Sequencing:

Ventral-cord enriched cDNAs were partially sequenced using pUC M13 and reverse M13 oligonucleotide primers (Promega) by the technique of Sanger et al. (Sanger, F., Nicklen, S. and Coulson, A. R., "DNA Sequencing With Chain Terminating Inhibitors," *Proc.Natl.Acad.Sci. U.S.A.* 74:5463–5468 (1977), incorporated herein by reference in its entirety, using an automated sequencer (Applied Biosciences Inc., Norwalk, Conn.) and using a $^{35}$S-dATP (ICN Pharmaceuticals, Inc., Irvine, Calif.) and Sequenase (U.S. USB™ Biochemicals Corporation, Cleveland, Ohio). Complete sequences of the isolated cDNAs were determined using nested deletions (Pharmacia). Oligonucleotide primers were synthesized, in a DNA synthesizer (Applied Biosciences Inc.) and used to fill in sequence gaps. These sequences were compared to known sequences using the University of Wisconsin Computer Program Package provided by GenBank.

(d) Northern Blot Analysis:

Total RNA was prepared from different brain regions as well as from various peripheral tissues and 10 µg/lane were separated in 1% denaturing agarose gels, transferred to Hybond Nylon membranes, and irreversibly fixed by incubating filters at 80° C. for 2 hr. Prehybridization and hybridization were performed at 65° C. in solutions containing 7.5% SDS, 0.5 M phosphate buffer (pH 7.0), 1 mM EDTA, and 1% bovine serum albumin. [$^{32}$P]-labeled cDNA probes were generated by isolating cDNA from plasmid DNA and using random primers according to the manufacturer's protocol (Amersham). After hybridization, the membranes were washed with 0.2×SSC and 0.1% SDS at 61° C. prior to exposure to X-ray film. Blots were stripped with 0.1% SDS at 100° C. for 15 minutes and reprobed with [$^{32}$P]-labeled tubulin cDNA in order to control for gel loading and RNA integrity. Quantitation of autoradiogram densities was determined using a LKB densitometer (Pharmacia).

(e) In Situ Hybridization:

In situ hybridization was performed using $^{35}$S-labeled cRNA probes by the method of Angerer et al. (Angerer, L. M., Stoler, M. H., and Angerer, R. C., "In Situ Hybridization With RNA Probes: An Annotated Recipe." In K. L. Valentino, J. H. Eberwine, and J. D. Barches (Eds) "In Situ Hybridization," Oxford University Press 43–70 (1987), incorporated herein by reference in its entirety) as modified by Popper et al. (Popper, P., Ulibarri, C., and Micevych, P. E., "The Role of Target Muscles in the Expression of Calcitonin Gene-Related Peptide mRNA in the Spinal Nucleus of the Bulbocavernosus," Mol.Brain.Res. 13:43–51 (1992), incorporated herein by reference in its entirety). Oligodendrocyte cultures were enriched according to the method of Suzumura et al. (Suzumura, A., Bhat, S., Eccleston, P. A. et al., "The Isolation and Long-Term Culture of Oligodendrocytes From Newborn Mouse Brain," Brain Res. 324:379–383 (1984), incorporated herein by reference in its entirety). These cells were treated in a similar manner as brain slices for in situ hybridization.

(f) Western Blot Analysis and Immunohistochemistry:

Polyclonal antibodies were raised against a 16 amino acid synthetic peptide (oligodendrocyte-specific protein peptide 179–194 of SEQ ID NO:2) conjugated to Keyhole Limpet Protein Antigen (available from Pierce, Rockford, Ill. and Research Genetics, Huntsville, Ala.). (This sequence was chosen for potential antigenicity according to criteria understood by those with skill in the art, including 1) hydrophobicity, 2) relation to the C terminus, and 3) lack of homology with other known sequences, among others. However, this sequence did not eventually provide an epitope recognized by the patient antibodies from actual patient samples.) The IgG fraction was isolated from sera using protein-A sepharose (Zymed Laboratories Inc., South San Francisco, Calif.) and concentrated using a Centricell® 20 concentrator (Polysciences, Inc., Warrington, Pa.) Thirty μg of rat brain homogenate/lane were subjected to SDS/PAGE on 12% gels (Laeumili, U.K., "Cleavage Of Structural Proteins During the Assembly of the Head of Bacteriophage T4." Nature 227 (259); 680–5 (1970), incorporated herein by reference in its entirety) and electrophoretically transblotted onto nitrocellulose paper. Immunoblots and immunohistochemistry were performed according to the method of Bronstein, et al. (Bronstein, J. M., Wasterlain, C. G., Lasher, R., Bok D., Farber, D. B., "Localization of Retinal Calmodulin Kinase," Exp Eye Res. 47:391–402 (1988), incorporated herein by reference in its entirety) using antibody dilutions of 1:100 and 1:1000, respectively. Antibody specificity was confirmed by pre-incubating the antibody with 100 μg/ml oligodendrocyte-specific protein peptide 179–194, for 3 hrs. prior to incubation with nitrocellulose paper or tissue.

(g) Cell Culture and Transfection:

3T3 fibroblast cells were maintained in Dulbecco's modified Eagle's medium containing 10% fetal calf serum in 5% $CO_2$. A 1.7 Kb fragment containing the open reading frame and a 2.3 Kb containing the complete myelin basic protein (GenBank Accession #M15060) cDNA, were inserted into the pBabepuro retroviral expression vector (H. Land, Impe-rial Cancer Research Fund, London). These constructs and pBabepuro alone (as control) were then transfected into 3T3 fibroblasts using DOTAP (Boehringer Mannheim, GMBH, Indianapolis, Ind.) according to Boehringer's protocol, the manufacturer of DOTAP, incorporated herein by reference in its entirety. Stable transformants were selected by adding 2.5 μg/ml puromycin (Sigma Chemical Co., St. Louis, Mo.) to culture media, passaged at identical concentrations, and maintained for 2 weeks in puromycin. Growth rates were estimated by incubating the transformants with $^3$H-thymidine (1 μCi/ml) for 12 hours, washing the cells with PBS, precipitating the DNA with 5% TCA, solubilizing in 0.2M NaOH/0.1%SDS, and counting aliquots in a liquid scintillation counter. Proliferation experiments were performed 3 times in triplicate.

II. MURINE OLIGODENDROCYTE-SPECIFIC PROTEIN AND cDNA SEQUENCE ANALYSIS AND PREDICTED STRUCTURE

Using the technique disclosed above, we employed subtractive hybridization to generate myelin-enriched probes which were then used to screen a spinal cord cDNA library. An approximately 1.9 Kb cDNA was isolated and both strands were sequenced. The complete cDNA contained 1801 nucleotide with an open reading frame of 621 nucleotide and a 1018 base pair 3' untranslated region as shown in FIG. 1, SEQ ID NO:1. A canonical AAUAAA polyadenylation signal was identified at position 1776 and the poly A tail was limited to 9 A residues. A GenBank database search of the complete nucleotide sequence revealed no significant homology with any previously reported genes.

As shown further in FIG. 1, the deduced amino acid sequence of oligodendrocyte-specific protein contained 207 amino acid residues with a predicted molecular mass of 22.1 kDa. No consensus glycosylation sites (Asn XX Thr/Ser) were identified. A PROFILE analysis (Gribskov, M., McLachlan, A. D., and Eisenberg, D., "Profile Analysis: Detection of Distantly Related Proteins," Proc.Natl.Acad. Sci. 84:4355–4358 (1987), incorporated herein by reference in its entirety) of the deduced amino acid sequence was performed. PROFILE analysis takes in account selection pressure in addition to sequence similarities and gaps in determining if two (or more) proteins might have common ancestry. The PROFILE analysis showed significant homology with murine PMP-22, SEQ ID NO:3, with 48% amino acid similarity and 21% identity (z value of 5.3 standard deviation units). This analysis suggests that the two proteins are related (in general, z values>4.5 are indicative of related proteins).

Referring now to FIG. 2, there is illustrated a comparison between mouse PMP-22, SEQ ID NO:3, (upper rows) and oligodendrocyte-specific protein (lower rows) amino acid sequences. Identical amino acids are denoted by vertical lines. Positive amino acid relationships are denoted by a colon, zero-value relationships by a period, and negative relationships by no markings. These relationships are defined by the PAM250 (percent accepted mutation) scoring matrix used in standard sequence alignment programs. Positive relationships indicate a higher probability that the residues are evolutionarily related, whereas negative relationships indicate a higher probability for a chance mutation. The asterisk denotes position 150 which is the residue replaced in the trembler mouse in mouse PMP-22.

Four hydrophobic regions were predicted using the method of Kyte and Doolittle (Kyte, J. and Doolittle, R. F., "A Simple Method for Displaying the Hydropathic Character of a Protein," J.Mol.Biol. 157:105–132 (1982), incorporated herein by reference in its entirety). As can be seen in FIG. 2, the four predicted hydrophobic regions of oligodendrocyte-specific protein were homologous with the four hydrophobic regions of PMP-22. The four hydrophobic regions of both sequences are highlighted by under and over lining.

Referring now to FIG. 3, there is illustrated the predicted structure of oligodendrocyte-specific protein, SEQ ID NO:2, and PMP-22, SEQ ID NO:3. Basic and acidic amino acid residues are represented by a plus and a minus respectively. The glycine residue at position 150 is blackened. Four potential transmembrane domains of oligodendrocyte-specific protein were identified by analysis of hydrophobic moments (Eisenberg, D., Schwarz, E. Komaromy, M., and Wall, R., "Analysis of Membrane and Surface Protein Sequences With the Hydrophobic Moment Plot," *J.Mol. Biol.* 179:125–142 (1984), incorporated herein by reference in its entirety). As shown in FIG. 3, the identified four potential transmembrane domains show a marked similarity of oligodendrocyte-specific protein conformation to that of PMP-22. The three gaps in amino acid sequence alignment shown in FIG. 2 are all in nontransmembrane domains and such non-transmembrane domains are often less functionally significant. Therefore, it appears that oligodendrocyte-specific protein and PMP-22 share functional attributes by virtue of their structural similarities.

Further, the fact that oligodendrocyte-specific protein and PMP-22 have four potential membrane domains implies that these domains are functionally important enough to withstand evolutionary pressures in addition to sequence similarities and gaps in determining if two (or more) proteins might have common ancestry. This selection pressure would pose a bias towards identity and similarity of hydrophobic amino acids within these regions.

Although a z value of 5.3 obtained by the PROFILE analysis by itself is not sufficient to establish that the two proteins are related, the relationship of PMP-22 and oligodendrocyte-specific protein is supported by the additional information that they are both expressed in cells that myelinate neurons (see below) and that their predicted structures are remarkably similar. Also, the glycine residue at position 150 of PMP-22 (fourth transmembrane domain) is conserved in oligodendrocyte-specific protein. Replacement of this residue in PMP-22 with an aspartic acid, FIG. 3, results in the mouse trembler phenotype. It is possible that replacing this equivalent glycine residue with aspartate in oligodendrocyte-specific protein would also result in abnormal myelination.

III. LOCALIZATION OF MURINE OLIGODENDROCYTE-SPECIFIC PROTEIN EXPRESSION

Radiolabeled oligodendrocyte-specific protein cDNA was used to probe Northern blots of developing mouse spinal cord RNA and of a variety of 6–8 week old fetal mouse tissues lung, skeletal muscle, kidney, spleen, and heart as follows. Ten μg total RNA/lane from the various tissues were separated in a 1% denaturing agarose gel, immobilized to nylon membrane, and hybridized with [$^{32}$P]-labeled oligodendrocyte-specific protein cDNA. After washing, the membrane was exposed to X-ray film at 80° C. for 36 hrs. autoradiography. The blot was stripped and reprobed with tubulin cDNA. Optical densities of autoradiograms were measured and the image shown is normalized to tubulin hybridization to control for the amount of RNA in each lane.

Figure 4:
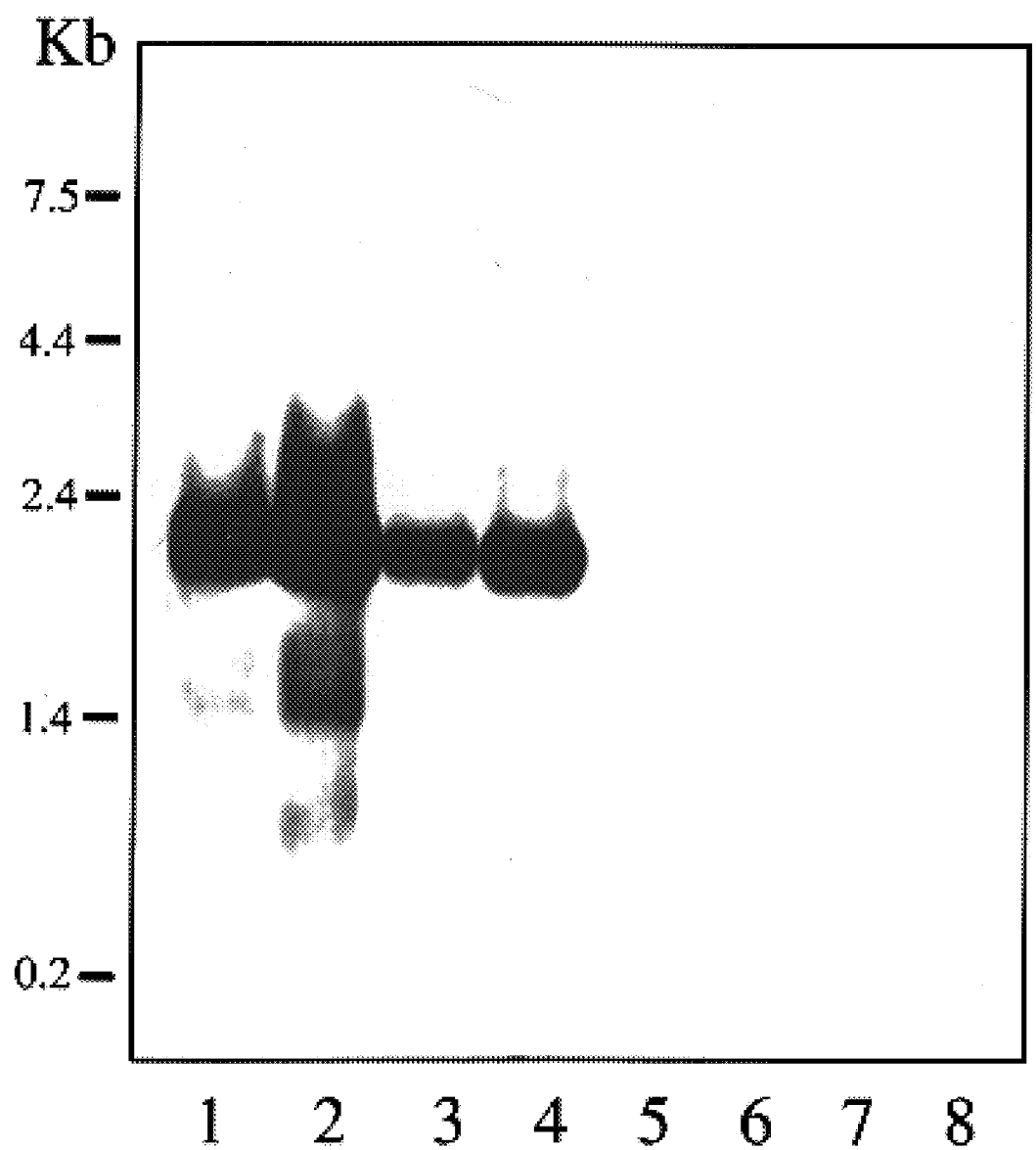
FIG. 4 illustrates a Northern blot analysis of oligodendrocyte-specific protein RNA.

The results are shown in FIG. 4. As can be seen, a major 2.1 Kb transcript was detected in dorsal spinal cord (lane 1), ventral spinal cord (lane 2), cerebral cortex (lane 3), and cerebellum (lane 4), that is tissues of the central nervous system, but not in sciatic nerve (lane 5), liver (lane 6), lung (lane 7), skeletal muscle (lane 8), kidney, heart, or spleen (not shown). A minor 1.5 Kb transcript was observed in cortex and spinal cord samples.

Figure 5A:
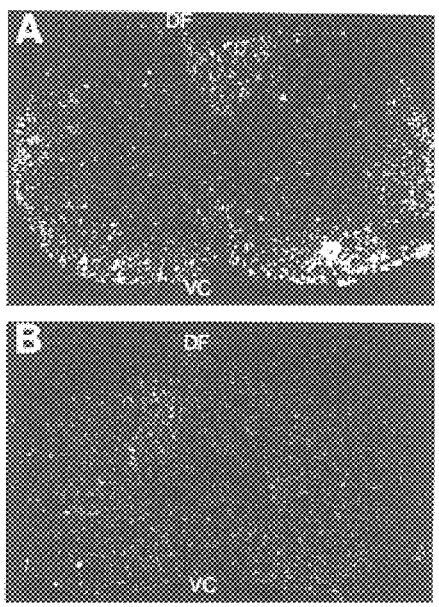
Figure 5B:
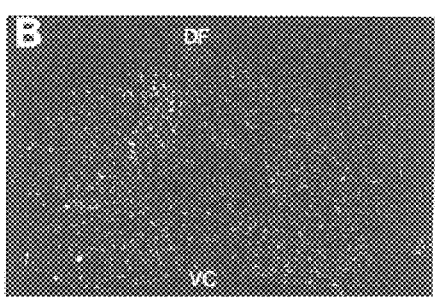

In situ hybridization was performed to determine the cellular localization of oligodendrocyte-specific protein expression, i.e. mRNA. 35S-riboprobes were generated using linearized plasmid-cDNA as templates from both strands and were hybridized to 30–40 day-old mouse brain and spinal cord. Dark field photomicrographs of the results are shown in FIGS. 5A–F, where "df"=dorsal fasciculus; "vc"=ventral columns; "cc"=corpus callosum; and "ac"= anterior commissure. FIGS. 5A and 5B show mouse spinal cord, 5C and 5E show mouse brain, and 5D and 5F show isolated oligodendrocyte cultures. Referring to FIG. 5, it can be seen that oligodendrocyte-specific protein antisense riboprobe hybridized predominantly to cells in white matter tracts which appeared to be oligodendrocytes, FIGS. 5A–D.

The identity of these cells stained by oligodendrocyte-specific protein riboprobe was supported by performing in situ hybridization in adjacent sections using a PLP riboprobe, which revealed a substantially identical staining pattern as shown in FIGS. 5C and 5E. Furthermore, oligodendrocyte-specific protein RNA was highly expressed in the majority of cells in an enriched oligodendrocyte cell culture containing greater than 90% oligodendrocyte, as shown in FIG. 5D. Also, sense strand riboprobe generated from anti-sense strand cDNA was not observed to have specific hybridization as shown in FIGS. 5B and F. This indicates that cellular hybridization obtained with the anti-sense probe was specific for oligodendrocyte-specific protein mRNA.

Figure 6:
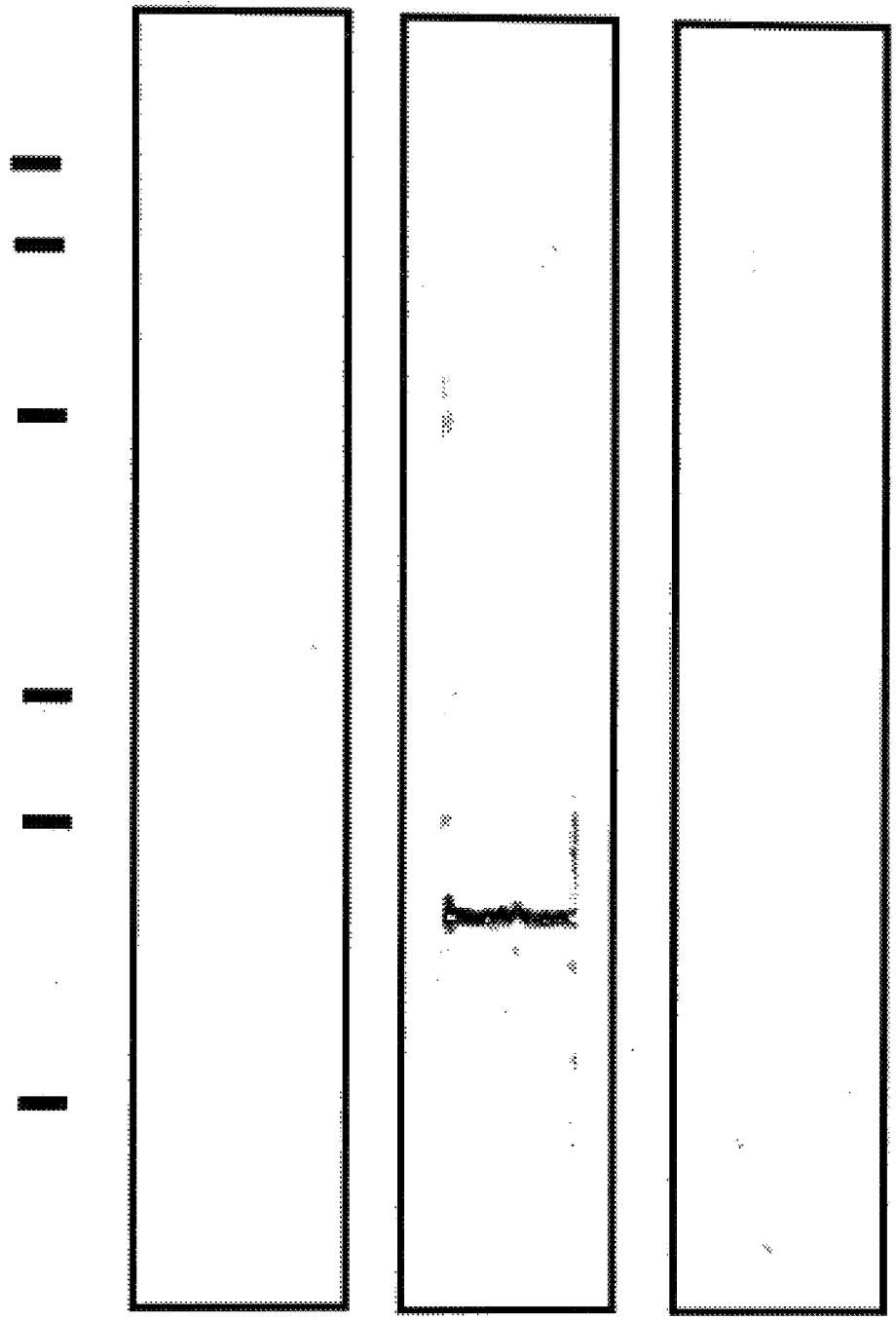
FIG. 6 illustrates an immunoblot of rat brain homogenates.

In order to demonstrate the presence of oligodendrocyte-specific protein in rat brain homogenate, polyclonal antibodies were raised against a sixteen amino acid synthetic peptide, oligodendrocyte-specific protein peptide 179–194, corresponding to part of the C-terminal end of oligodendrocyte-specific protein. FIG. 6 is an immunoblot of the rat brain homogenates illustrating the resultant reactions using the polyclonal antibodies. Lane 1 was incubated with pre-immune IgG. Lane 2 was incubated with an anti-OSP peptide antibody (1:100 dilution). Lane 3 was incubated with anti-OSP peptide antibody which was pre-absorbed with oligodendrocyte-specific protein peptide. Positions of molecular weight standards (200, 97, 68, 43, 29, and 18 kDa from top to bottom, respectively), are shown to the left of lane 1. As can be seen in lane 2 of FIG. 6, one band of apparent molecular mass of approximately 22 kDa was observed when blots were incubated with immune IgG only. However, no staining was observed using pre-immune IgG, lane 1, or when the antibody was pre-incubated with the peptide antigen, lane 3.

Figure 7A:
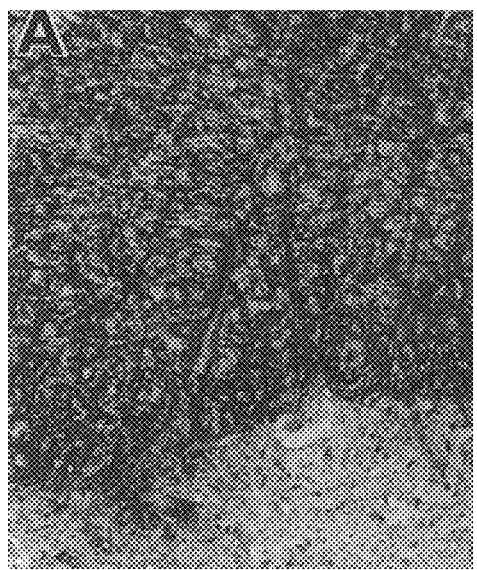
FIGS. 7A–7D illustrate the immunocytochemistry of rat spinal cord using anti-OSP antibody, 7A and anti-MBP antibody, 7B and controls, 7C and 7D.
Figure 7B:
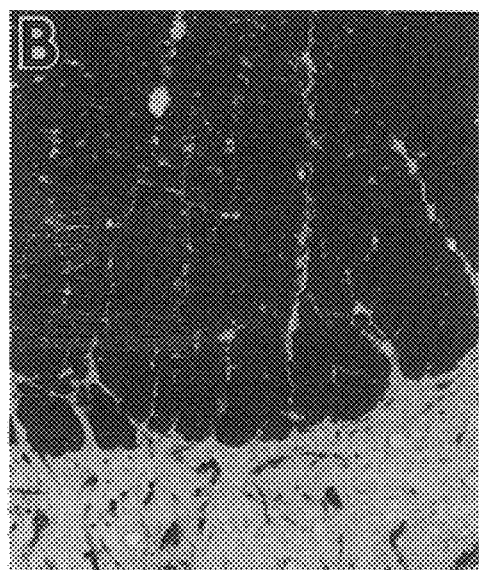
Figure 7C:
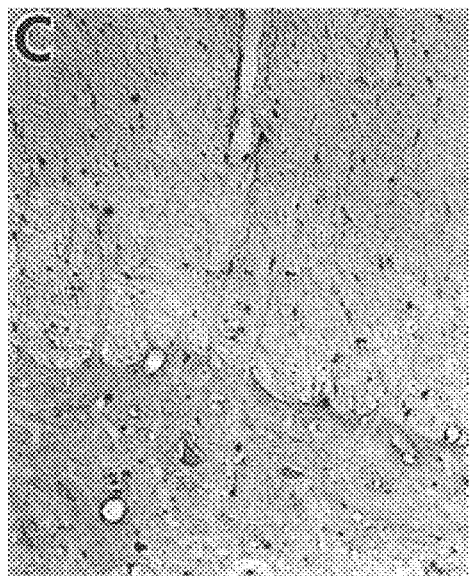
Figure 7D:
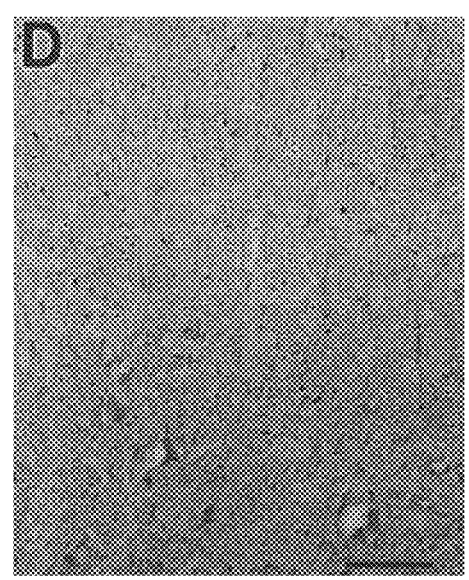

Referring now to FIG. 7, there is illustrated an immunocytochemistry study of rat spinal cord using anti-OSP antibody, FIG. 7A and anti-MBP antibody, FIG. 7B performed in order to demonstrate the localization of oligodendrocyte-specific protein to myelin containing areas of the central nervous system. As can be seen, light microscopic immunocytochemistry localized oligodendrocyte-specific protein to white matter tracts of the ventral funiculus of the spinal cord when incubated with anti-OSP antibody, FIG. 7A, with little signal in the gray matter of rat spinal cord. This pattern is consistent with in situ hybridization patterns. Although the identity of all cells stained could not be ascertained, the staining pattern was similar to that of MBP performed in adjacent sections, FIG. 7B, providing further support to the observation that oligodendrocyte-specific protein is expressed predominantly by oligodendrocytes and is present in myelin. No specific staining was observed using pre-immune serum, FIG. 7C, or using an anti-OSP antibody pre-absorbed with oligodendrocyte-specific protein peptide, FIG. 7D.

IV. DEVELOPMENTAL EXPRESSION OF OLIGODENDROCYTE-SPECIFIC PROTEIN AND INDUCTION OF GROWTH ARREST

Expression of PMP-22 is known to be developmentally regulated and is believed to modulate Schwann cell proliferation. (Chance P. F., Alderson M. K., Leppig K. A., et al., "DNA deletion associated with liability to pressure palsies," Cell 72:143–15 (1993); Welcher A. A., Suter, U., De Leon, M., Snipes G. J., and Shooter, E. M. "A myelin protein is encoded by the homologue of a growth arrest-specific gene," Proc.Nad.Acad. Sci. U.S.A. 88:7195–7199 (1991); Yoshikawa H., Nishimura T., Nakatsuji Y., Fujimura H., Himoro M., Hayasaka K., Sakoda S., and Yanagihara T., "Elevated Expression of messenger RNA for peripheral myelin protein 22 in biopsied peripheral nerves of patients with Charcot-Marie-Tooth Disease type 1A," Ann.Neurol. 35:445–450 (1994), each incorporated herein by reference in its entirety). In order to determine if oligodendrocyte-specific protein plays a similar role in oligodendrocytes, we studied the developmental expression of oligodendrocyte-specific protein in the central nervous system by Northern blot analysis and the effect of enhanced expression on proliferation rates in culture.

Figure 8A:
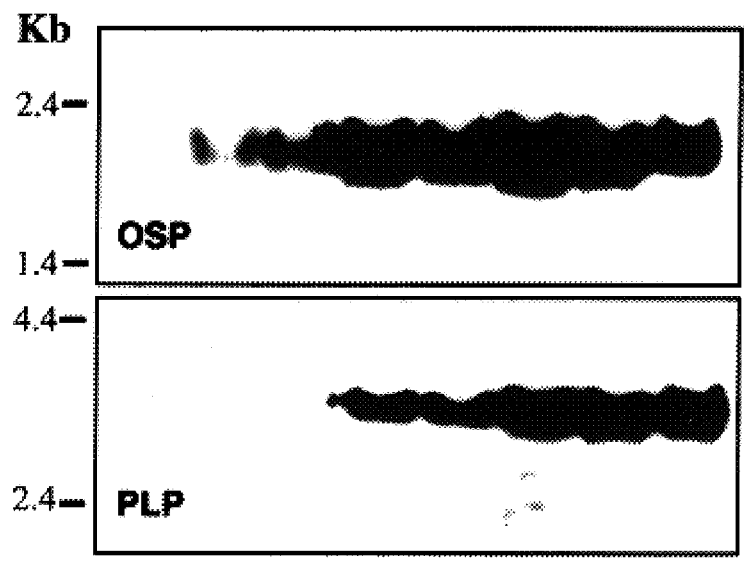
FIGS. 8A–8B illustrate a comparison between the developmental expression of oligodendrocyte-specific protein and proteolipid protein using a Northern blot, FIG. 8A and optical densities of the sample, FIG. 8B.
Figure 8B:
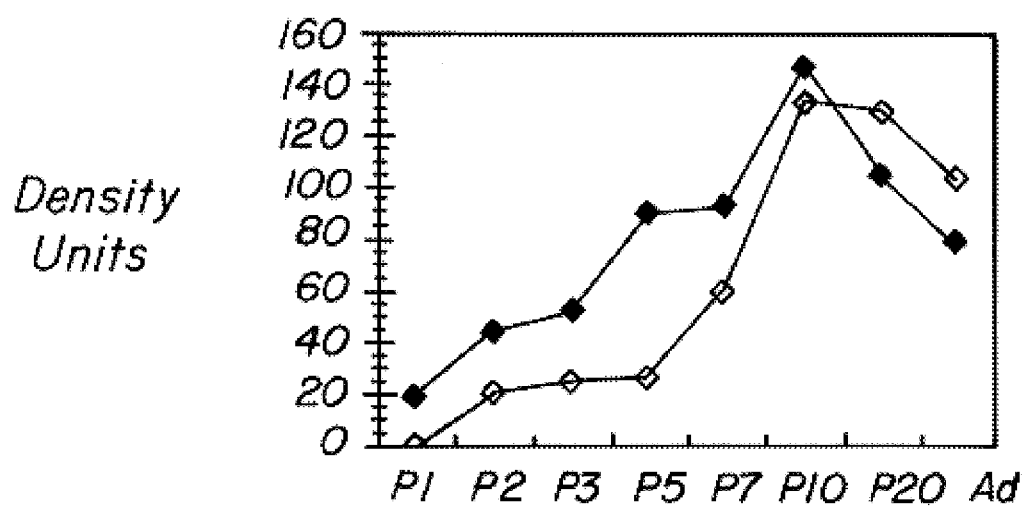

Referring now to FIG. 8, there is illustrated a Northern blot analysis, FIG. 8A, using 10 μg total RNA isolated from the spinal cords of mice at different postnatal ages. "P1"= postnatal day 1; "P2"=postnatal day 2, "P3"=postnatal day 3; "P5"=postnatal day 5; "P7"=postnatal day 7; "P10"= postnatal day 10; "P20"=postnatal day 20; and "Ad"=adult mice. The RNA were electrophoresed on 1% agarose gels, transferred to a nylon membrane, and hybridized with oligodendrocyte-specific protein and proteolipid protein cDNA sequentially on the same blot as described above. Optical densities of the obtained signals were measured and plotted resulting in FIG. 8B. Solid squares represent oligodendrocyte-specific protein hybridization and open squares represent PLP hybridization.

As can be seen in FIGS. 8A and 8B, oligodendrocyte-specific protein mRNA (upper portion of FIG. 8A and solid squares of FIG. 8B) was first detectable in a mouse spinal cord at postnatal day 2, peaked at postnatal day 10, and declined thereafter. This pattern was compared with the pattern for proteolipid protein (lower portion of FIG. 8A and open squares of FIG. 8B) and was found to be similar except that proteolipid protein expression began slightly later and remained elevated until postnatal day 20 before tailing off. Therefore, it appears that oligodendrocyte-specific protein has a developmental expression similar to proteolipid protein.

Figure 9A:
FIGS. 9A–9D illustrate the immunocytochemistry of 3T3 cells transfected with oligodendrocyte-specific protein FIGS. 9A and 9B, and transfected with MBP cDNA, FIGS. 9C and 9D.
Figure 9B:
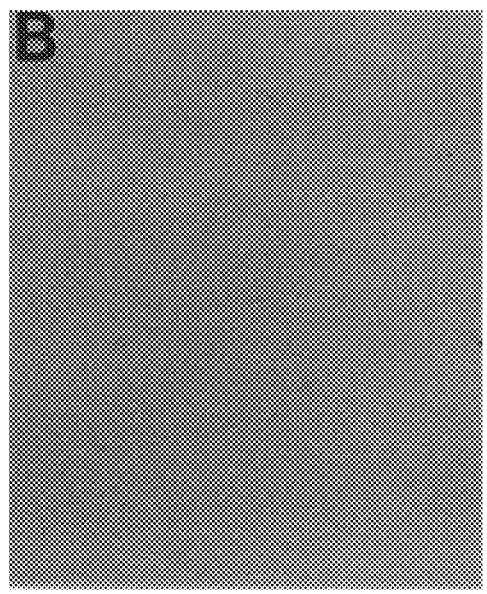
Figure 9C:
Figure 9D:
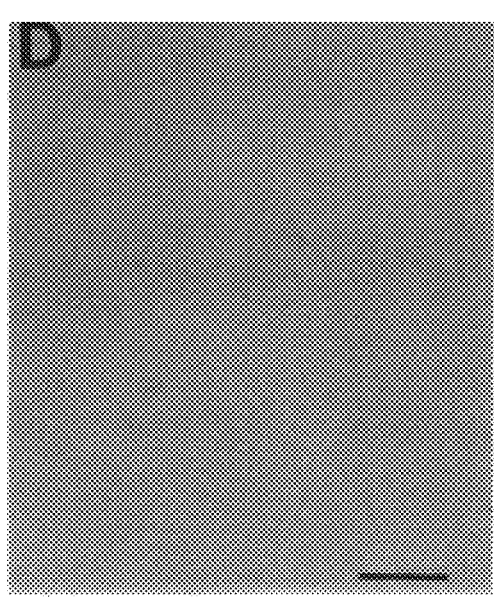

PMP-22 expression is increased in 3T3 fibroblast cells during growth arrest (Welcher A. A., Suter, U., De Leon, M., Snipres G. J., and Shooter, E. M., "A myelin protein is encoded by the homologue of a growth arrest-specific gene," Proc.Nad.Acad.Sci. U.S.A. 88:7195–7199 (1991)), and inhibits growth when over-expressed in Schwann cells as well as promoting Schwann cell growth when under-expressed (Zoidl G., Blass-Kampmann S., D'Urso D., Schmalenbach C., Muller, H. W., "Retroviral-mediated gene transfer of the peripheral myelin protein PMP-22 in Schwann cells: modulation of cell growth," Embo Journal 14(6):1122–8 (1995) incorporated herein by reference in its entirety). In order to determine if oligodendrocyte-specific protein had similar effects, we expressed oligodendrocyte-specific protein in 3T3 cells to evaluate its effect on proliferation of these cells. 3T3 cells were transfected with the retroviral expression vector pBabepuro, with vector containing oligodendrocyte-specific protein cDNA, FIGS. 9A and 9B, or with myelin basic protein cDNA, FIGS. 9C and 9D, and growth rates were estimated using H-thymidine incorporation, according to methods understood by those with skill in the art with reference to the disclosure herein.

The results are shown in FIG. 9. The majority of cells transfected with OSP cDNA, FIGS. 9A and 9B, and myelin basic protein cDNA, FIGS. 9C and 9D, stained only with their respective antibodies, FIGS. 9A and 9C respectively, confirming that oligodendrocyte-specific protein and MBP were expressed and that there is no detectable levels of these myelin proteins in untransfected 3T3 cells.

Further, expression of oligodendrocyte-specific protein resulted in a 43% decrease in H-thymidine incorporation compared to vector alone (p<0.01). Expression of MBP in 3T3 cells had no effect on growth. Also, oligodendrocyte-specific protein mRNA was not present in cells transfected with vector alone or vector-MBP cDNA but was easily detectable by Northern blot analysis in cells transfected with vector-OSP cDNA (data not shown). While it is possible that these results could be secondary to nonspecific inhibition by expression of a hydrophobic protein, the fact that expression of MBP had no effect on proliferation rates in 3T3 cells supports a specific mechanism.

Additionally, the effect of OSP on mouse glial growth and differentiation was demonstrated by showing that altering OSP gene dosage in a conditionally immortalized mouse glial cell line (CIMO) had a profound effect on cellular proliferation.

CIMOs grow rapidly at 33° C. conditions due to the activity of the SV40 ts58 antigen but grow slowly at 37° C. OSP expression was found to be 10 fold higher in CIMOs growing rapidly at 33° C. compared to CIMOs growing slowly at 37° C. Over-expression of OSP (stabely transfected cells) had little effect on CIMO growth at 33° C. but increased $^3$H-thymidine incorporation 82 fold when cells were grown at 37° C. (twice the effect of the ts58 antigen). (data not shown)

Therefore, oligodendrocyte-specific protein shares not only similarities in sequence and structure but oligodendrocyte-specific protein may also be involved in the regulation of central nervous system oligodendrocyte proliferation in a similar manner as PMP-22 appears to regulate Schwann cell growth in the peripheral nervous system. Because of the similarities between oligodendrocyte-specific protein and PMP-22, oligodendrocyte-specific protein is a likely candidate for the central nervous system homologue to PMP-22.

V. DETERMINATION OF HUMAN OLIGODENDROCYTE-SPECIFIC PROTEIN cDNA SEQUENCE AND HUMAN OLIGODENDROCYTE-SPECIFIC PROTEIN SEQUENCE

The human oligodendrocyte-specific protein (hOSP) cDNA sequence was determined as follows. A human gt11 spinal cord cDNA library was obtained from Dr. A. Campagnoni (University of California at Los Angeles, Los Angeles, Calif., United States) and was screened with a mouse [$^{32}$P]-labeled OSP ORF (open reading frame) cDNA probe. Seven positive clones were identified in 1×10$^6$ plagues and the clone containing the largest insert, a 2.3 Kb fragment, was isolated. The cDNA was then subcloned into pGEM 7f-((Promega, Corporation, Madison, Wis.) and sequenced.

The resultant sequence, SEQ ID NO:4, human OSP cDNA contains 2243 nucleotides. It is 52% identical to murine OSP and has 85% identity in the open reading frame. As can be appreciated by comparing SEQ ID NO:1 to SEQ ID NO:4, the 1.4 Kb 3' untranslated region of SEQ ID NO:4 is only about 50% identical to the corresponding region of SEQ ID NO:1.

Referring now to SEQ ID NO:5, there is shown the deduced amino acid sequence of human oligodendrocyte-specific protein. The sequence contains 218 amino acids having a predicted molecular mass of 23 kDa and four predicted transmembrane domains. The amino acid sequence is 86% identical to murine oligodendrocyte-specific protein. Further, residues 115–124 of murine OSP, SEQ ID NO:2, are identical to residues 115–124 human OSP, SEQ ID NO:5.

VI. LOCALIZATION OF HUMAN OSP

Figure 10:
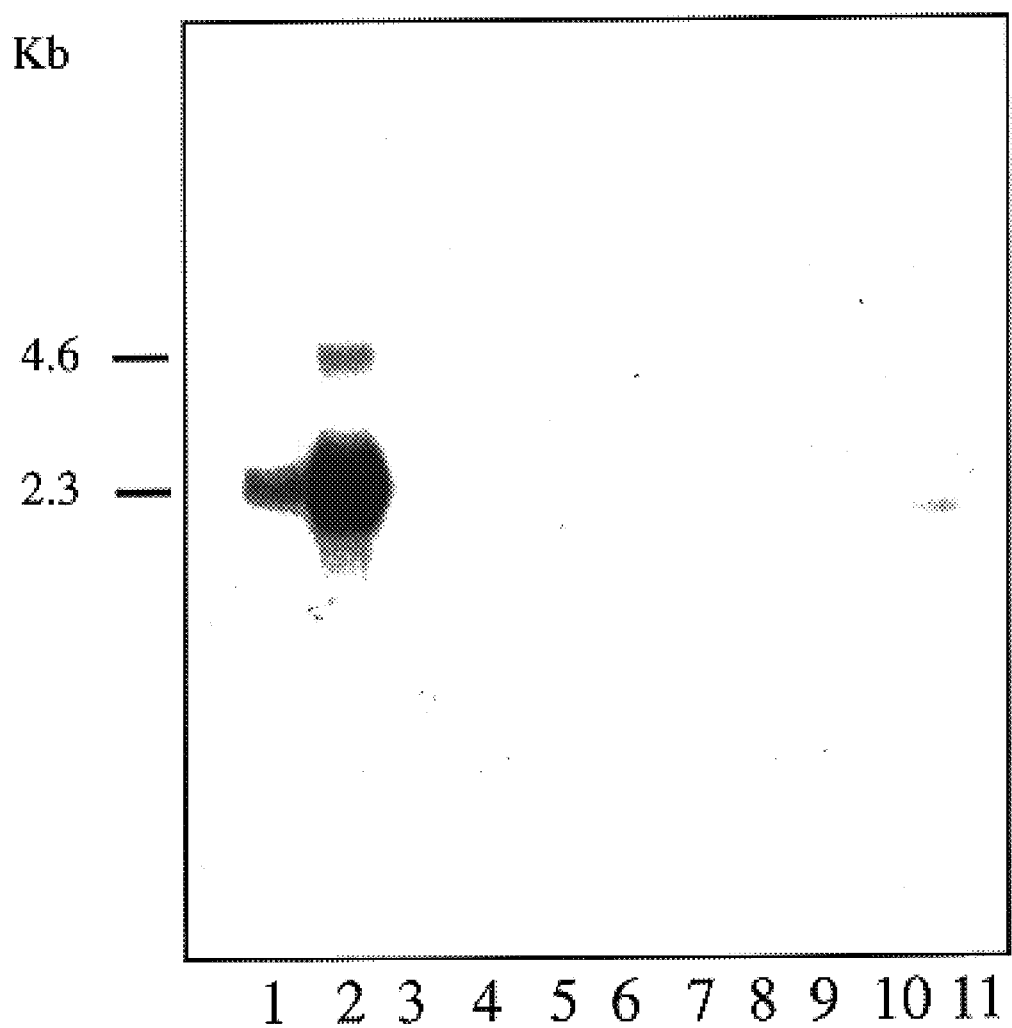
FIG. 10 illustrates tissue localization of human OSP RNA transcript was determined by Northern blot analysis performed on total RNA isolated from various tissues of a 16 year old deceased male within 8 hours of death.

Tissue localization of human OSP RNA transcript was determined by Northern blot analysis performed on total RNA isolated from various tissues of a 16 year old deceased male within 8 hours of death. Referring now to FIG. 10, the results are shown for 10 µg total RNA per lane for skeletal muscle (lane 1), brain (lane 2), testes (lane 3), heart (lane 4), kidney (lane 5), spleen (lane 6), lung (lane 7), pancreas (lane 8), liver (lane 9), adrenal gland (lane 10) and peripheral nerve (lane 11), from left to right, respectively. As can be seen, there is a major 2.3 kDa OSP transcript predominantly in the brain, with lesser amounts in skeletal muscle, testes and peripheral nerve. Additionally, there is a less prominent 4.6 kDa transcript detected in the brain only.

VII. FURTHER DESCRIPTION OF EMBODIMENTS OF THE PRESENT INVENTION

According to the present invention, therefore, there is also provided a protein consisting essentially of purified oligodendrocyte-specific protein or purified biologically active variants thereof, or a combination of purified oligodendrocyte-specific protein and biologically active variants thereof. This protein can be purified from natural sources such as mouse, rat or human, or can be made by recombinant techniques as will be understood by those with skill in the art with reference to the disclosure herein. Further, there is provided a protein recognized by a monoclonal antibody having affinity to oligodendrocyte-specific protein or a variant of oligodendrocyte-specific protein.

Still further, there is provided a DNA sequence encoding for oligodendrocyte-specific protein or its biological variants, or its complementary strands. The invention also provides a DNA sequence which hybridizes to a DNA such a DNA sequence.

Also, there is provided a high affinity monoclonal antibody which immunoreacts with oligodendrocyte-specific protein or to a fragment thereof. The antibody can have an Fc portion selected from the group consisting of the IgM class, the IgG class and the IgA class.

There is also provided a method of making a monoclonal antibody which immunoreacts with oligodendrocyte-specific protein comprising the steps of, first, administering to a host oligodendrocyte-specific protein in an amount sufficient to induce the production of antibodies to the oligodendrocyte-specific protein from the antibody-producing cells; second, recovering the antibody-producing cells from the host; third, forming cell hybrids by fusing the antibody-producing cell to cells capable of substantially unlimited reproduction; fourth, culturing the hybrids; and, fifth collecting the monoclonal antibodies as a product of the hybrids.

There is also provided a vector containing a DNA molecule encoding oligodendrocyte-specific protein, as well as a prokaryotic or eukaryotic host cell stably transformed or transfected by the vector, made according to techniques understood by those with skill in the art with reference to the disclosure herein Further, there is provided a method of making the oligodendrocyte-specific protein or its biological variants comprising the steps of, first, culturing a microorganism transformed with DNA encoding for oligodendrocyte-specific protein; and then, recovering the oligodendrocyte-specific protein or its complementary strands.

VIII. DEVICE HAVING MULTIPLE PEPTIDE SPOTS FOR THE DETERMINATION OF IMMUNOREACTIVE REGIONS OF A PROTEIN

According to another aspect of the present invention, there is provided a device for, among other uses, identifying an epitope region of a peptide, protein, or protein homologue of interest, where the peptide, protein, or protein homologue of interest has a known amino acid sequence. The device comprises a polypropylene membrane or "support" having a plurality of sequentially oriented peptide spots which resist diffusion, compression, clogging and fouling. Each peptide spot contains a peptide having an amino acid sequence and the amino acid sequence of the peptides contained on the sequentially oriented peptide spots sequentially progress through the amino acid sequence of the peptide, protein, or protein homologue of interest. The present invention further includes a method of making and a method of using the device.

The use of polypropylene for the membrane or support is advantageous over conventionally known materials for a number or reasons. First, polypropylene membranes are considerably cheaper than membranes of conventional material. Second polypropylene membrane are more resistant to solvents used in the processes disclosed herein. Therefore, there is less waste of material through inadvertent destruction of the support material. Third, polypropylene membrane give better signal to noise ratios than do conventional materials yielding a cleaner signal.

The technique of making the device involves synthesizing peptide spots on the surface of a polypropylene membrane. In a preferred embodiment, the support is a stable, derivatized, synthetic polypropylene membrane that is chemically modified to expose free amines (amine modified polypropylene) (available from Perseptive Biosystems, Inc., Framingham, Mass.) The polypropylene membrane is available in sheets of nine by twelve (9×12) inches. While it can be used in this size, we prefer to cut sheets of three and a half by four and a half (3.5×4.5) inches to save costs.

Peptide synthesis occurs by treating the polypropylene material to a predetermined number of synthesis cycles. Each synthesis cycle comprises the following steps: 1) Deprotection; 2) Pre-coupling Wash; 3) Coupling; and 4) Post-coupling Wash as disclosed herein. The number of amino acid residues per spot is determined by the number of cycles; each cycle resulting in one residue per peptide. For example, ten cycles results in a ten residue peptide.

The device can be made by, first, providing polypropylene membrane, as disclosed above, having dimensions of 3.5"× 4.5" in standard 96-well plate format, that is 8×12 wells; 0.9 mm apart. Fmoc-6-aminohexanoic acid is dissolved in HOBt/NMP solution (0.53 M HOBt/NMP) to a concentration of 0.53 M. The dissolved Fmoc-6-aminohexanoic acid is coupled to ninety-six discreet spots on the membrane according to the following steps:

(a) placing 30 μl of Fmoc-6-aminohexanoic acid (available from Calbiochem-NovaBiochem, La Jolla, Calif.) on each spot;

(b) adding 10 μl of DIC (25% diisopropylcarbodiimide, available from Advanced Chemtech, Louisville, Ky.) to each spot;

(c) waiting 10 minutes;

(d) removing the fluid by vacuum filtration;

(e) adding 20 μl of DMF (dimethylformamide, available from Fisher Scientific, Pittsburgh, Pa.) to each spot;

(f) waiting 1 minute;

(g) removing the fluid by vacuum filtration;

(h) repeating steps (a) to (g) one time (i) adding 20 μl of DMF to each spot;

(j) waiting 1 minute;

(k) removing the fluid by vacuum filtration; and (l) repeating steps (i) to (k) three times The membrane is then immersed in pure acetic anhydride as a stripping agent (Fluka Chemika-Biochemika, Buchs, Switzerland) to acetylate the free amines and washed by adding 20 μl of DMF to each spot to remove the Fmoc from the Fmoc-6-aminohexanoic.

Next, peptides are added to the membrane according to the following synthesis cycle:

1) Deprotection:

(a) placing 25 μl PIP (25% piperidine) on each spot;

(b) waiting 10 minutes;

(c) removing the fluid by vacuum filtration;

2) Pre-coupling Wash;

(a) adding 20 μl of DMF;

(b) waiting 1 minute;

(c) removing the fluid by vacuum filtration;

(d) repeating steps (a) to (c) three times

3) Coupling;

(a) placing 30 μl of the desired derivatized amino acid (available from Calbiochem-NovaBiochem) on each spot (the amino acid will vary with each spot depending on the desired peptide per spot—see Example II);

(b) adding 10 μl of DIC to each spot;

(c) waiting 10 minutes;

(d) removing the fluid by vacuum filtration;

(e) adding 20 μl of DMF;

(f) waiting 1 minute;

(g) removing the fluid by vacuum filtration;

(h) repeating steps (a) to (g) one time

4) Post-coupling Wash;

(a) adding 20 μl of DMF to each spot;

(b) waiting 1 minute;

(c) removing the fluid by vacuum filtration; and (d) repeating steps (a) to (c) three times The derivatized amino acids used in step 3(a), above are listed in Table 1, as follows:

TABLE 1

| Name | One letter code | Three letter code | Derivative used |
| --- | --- | --- | --- |
| Alanine | A | Ala | Fmoc-Ala-OH |
| Arginine | R | Arg | Fmoc-Arg-(Pmc)-OH |
| Asparagine | N | Asn | Fmoc-Asn(Trt)-OH |
| Aspartic Acid | D | Asp | Fmoc-Asp(Otbu)-OH |
| Cysteine | C | Cys | Fmoc-Cys(Trt)-OH |
| Glutamic acid | E | Glu | Fmoc-Glu(Otbu)-OH |
| Glutamine | Q | Gln | Fmoc-Gln(Trt)-OH |
| Glycine | G | Gly | Fmoc-Gly-OH |
| Histidine | H | His | Fmoc-His(Boc)-OH |
| Isoleucine | I | Ile | Fmoc-Ile-OH |
| Leucine | L | Leu | Fmoc-Leu-OH |
| Lysine | K | Lys | Fmoc-Lys(Boc)-OH |
| Methionine | M | Met | Fmoc-Met-OH |
| Phenylalanine | F | Phe | Fmoc-Phe-OH |
| Proline | P | Pro | Fmoc-Pro-OH |
| Serine | S | Ser | Fmoc-Ser(tBu)-OH |
| Threonine | T | Thr | Fmoc-Thr(tBu)-OH |
| Tryptophan | W | Trp | Fmoc-Trp(Boc)-OH |
| Tyrosine | Y | Tyr | Fmoc-Tyr(tBu)-OH |
| Valine | V | Val | Fmoc-Val-OH |

One synthesis cycle is used for each amino acid residue desired. After performing a predetermined number of synthesis cycles, the Deprotection and Pre-coupling Wash steps are repeated in full.

Next, the polypropylene membrane is immersed in pure methanol (Fisher Scientific), soaked for five minutes, rinsed twice in methanol and air dried. Then, the membrane is placed under a fume hood and immersed in 50 ml of a 1:1 mixture of dichloromethane (Fisher Scientific) and Reagent R (95:2.5:1.5:1 of trifluoro acetic acid (Fisher Scientific), thioanisole (Aldrich Chemical Co., St. Louis, Mo.), ethanedithiol (Aldrich Chemical Co.) and anisole (Aldrich Chemical Co.) in a reaction dish (pyrex baking dish available from Corning Corp., Oneonta, N.Y.), covered by aluminum foil and gently rocked for one hour.

The result of the Deprotection step used in each synthesis cycle and the immersion in Reagent R is that the amino acids linked together through peptide bonds are in their natural form rather than a derivatized form used in Fmoc synthesis. Further, using this method of making the device results in peptides that are in a free-floating form, even though they are covalently bound to the support.

Finally, the membrane is removed from Reagent R and immersed in ethyl ether (Fisher Scientific) for five minutes to remove any side chains which might have formed. The membrane is then removed from the ethyl ether and air dried for about 5 minutes. The membrane is stored so constructed is stored in a plastic bag, such as a Ziplock® bag, until use.

IX. METHOD OF USING A DEVICE HAVING MULTIPLE PEPTIDE SPOTS FOR THE DETERMINATION OF IMMUNOREACTIVE REGIONS OF A PROTEIN

The first step in determining the immunoreactive regions of a peptide, protein or protein homologue of interest is to determine the amino acid sequence of the peptide or protein (or protein homologue). This can be done by reference to a data base or by sequencing techniques known to those with skill in the art.

Next, the peptide or protein of interest is synthesized in overlapping short peptides on a device having a series of peptide spots. Each spot contains peptides where the amino acid sequence of the peptides sequentially progress through the amino acid sequence of the peptide or protein of interest. In a preferred embodiment, the device for identifying the immunoreactive regions of a protein is the device comprising the polypropylene membrane as support according to the disclosure herein. Other devices comprising other materials as support are also available as will be understood by those with skill in the art with reference to the disclosure herein.

To construct the device, the amino acids which are to be synthesized on each spot of the device are calculated to ensure that each peptide shares equal and maximal overlap. The calculations can be performed manually or can be made by a computer program. Once the appropriate peptide sequences are determined, these peptides are synthesized on a device for identifying the immunoreactive regions of a protein according to the disclosure herein or in a manner equivalent to the method disclosed herein as will be understood by those with skill in the art with reference to the disclosure herein, After synthesizing the appropriate peptide sequences, the support is blocked by incubation for 1–2 hours in blocking buffer such as 1% BSA, or 5% non-fat dry milk powder, or 0.3% gelatin (each available from Sigma Chemical Co.). A primary antibody or antiserum to be used in determining the immunoreactive regions of the peptide is provided and is diluted in blocking buffer. A suitable dilution must be determined according to the manufacturer's specifications for western blotting or according to the disclosure herein as will be understood by those with skill in the art with reference to the disclosure herein, before adding it to the support. The diluted antibody or antiserum is incubated with the membrane on a shaker table for between about 2 hours and 18 hours. In a preferred embodiment, the incubation occurs overnight.

Next, the membrane is washed 3–6 times in a washing buffer such as tris-buffered saline or borate-buffered saline, having a pH between about 7.5–8.0 and containing 0.05% Tween-20® (each available from Sigma Chemical Co.). This leaves the primary antibody bound to the spots containing the immunoreactive sequences of the protein and washes away any non-specifically bound or absorbed antibody from non-immunoreactive spots and non-peptide modified regions of the membrane.

An enzyme labeled secondary antibody or biotinylated antibody and an enzyme labeled streptavidin having a suitable dilution is then added in blocking buffer. The suitable dilution must be determined by standard methods of Western blotting techniques as will be understood by those with skill in the art with reference to the disclosure herein. The support is again incubated with the membrane on a shaker table for between about 2 hours and 18 hours. In a preferred embodiment, the incubation is carried out overnight.

Next, the support is washed 3–6 times with wash buffer. The support is then removed from the buffer and transferred to a new container containing substrate appropriate to the secondary antibody as will be understood by those with skill in the art with reference to the disclosure herein, for example, nitroblue tetrazolium and bromo-cholorindolyl-phosphate (NBT/BCIP solution in 0.1 M carbonate buffer having a pH of about 9.5 (Sigma Chemical Co.) The support is kept in the container until the spots or bands are clearly visible or detectable by non-visual means. In a preferred embodiment, we use chromogenic substrates that can be read directly rather than chemiluminsecent or other substrates which can not be read directly. However, many types of substrates can be used as will be understood by those with skill in the art with reference to the disclosure herein. The support should be removed and dried before background staining levels are so high that they interfere with interpretation.

Membrane supports tend to be somewhat hydrophobic. We have found that the use of detergents such as Tween-20® and Triton X-100™ in the buffers to be useful wetting agents and that these non-ionic detergents also help prevent undesirable high levels of background staining.

Further, the immunoreactivity is often weak with the synthetic peptides bound to the support. In such cases, we have found that the increased sensitivity of enzyme chemiluminescence (ECL) can be helpful as will be understood by those with skill in the art with reference to the disclosure herein. Further, horse radish peroxidase (HRP) substrates can also be used to but they must be prepared fresh. Trimethyl benzidine (TMB) prediluted in buffers is a convenient substrate to use with HRP but the supports must be handled carefully to prevent smearing of the precipitated material.

With respect to the secondary antibody, enzyme conjugated secondary antibodies and streptavidin are available from a variety of sources. However, they are in general formulated for a high level of polymerization to optimize their performance in ELISA. Such high level of polymerization is not always optimal for immunoblotting according to the present invention. Therefore, we prefer to use conjugates which have been prepared and purified to a lower level of polymerization. Such preparations tend to lower background staining without compromising staining intensity. These are prepared as follows.

Autoantibodies can take several forms. Each of the antibody classes perform different function and the class distribution of antibodies in a patient sample could have clinical significance. For example, IgG antibodies are likely the most relevant class for tissue destructive disease. Our data was generated using IgG specific secondary antibodies. Class distribution that is predominantly IgM autoantibodies can be of low affinity and may not be physiologically relevant. Class distribution that is predominantly of the IgA class may reflect a tolerance induction and signal a remission of disease.

Human myeloma IgM, IgG and IgA of both light chain types are isolated from high titer patient sera and purified by conventional methods known to those with skill in the art. Briefly, IgM is precipitated either by dialysis in water, or by the addition of 6% polyethylene glycol 6000. IgG and IgA are precipitated by the addition of 2.0 M ammonium sulfate. The immunoglobulins are then chromatographed by gel filtration using either Sepharose 6B from IgM, or Sephacryl S-300/S-200 (Pharmacia/LKB) for IgG and IgA and monitored by measuring the absorbance at 280 nm. The appropriate elution fractions are then pooled, loaded onto DE-52 (Whatman, Inc., Clifton, N.J.), and eluted off with a linear gradient of 0.01 M to 0.2 M phosphate buffer having a pH of about 7.0. Appropriate fractions are evaluated for purity by SDS-PAGE, concentrated by ultrafiltration in a stirred cell (Amicon, Inc., Beverly, Mass.) and used as rabbit immunogens or immobilized on Sepharose 4B for affinity purification of antibody. Using such techniques, one can obtain purified human immunoglobulins including a variety of IgM's, IgG's and IgA's of both kappa and lambda light chain types, as well as IgD using equivalent techniques.

When cross-reactivity appears negligible, the antibodies are then affinity-purified on the columns of homologous proteins. The final purified material is then eluted off the column using low pH glycine-HCL buffers, neutralized, and concentrated. Each antibody is tested for specificity in both a direct and an indirect ELISA format using native and SDS-denatured (1% SDS, overnight at 37° C.) proteins. Anti-immunoglobulin antibodies are used only if their level of cross-reactivity is less than 1% in ELISA. Anti-human immunoglobulins are absorbed against collagen in order to lower background noise in the ELISA. They are purified twice on two different immunoglobulin proteins of the same heavy chain, but different light chain isotypes, in order to remove low level anti-idiotype contamination. These antibodies are also cross-absorbed against other human non-immunoglobulin proteins such as albumin and macroglobulins in order to further maximize their specificity.

With respect to the immunoassay reagent, the immunoassay can be formatted using either monoclonal antibody, polyclonal antibody, or a combination of the two and can incorporate either intact antibody, F(ab')2 fragments, or F(ab') fragments, or any combination of these. If F(ab')2 fragments are to be used, they are generated by dialyzing the antibodies into 0.1 M acetate buffer or 0.1 M formic acid buffer at pH 3.5–4.5, adding pepsin at a ratio of 2–3 mg per 100 mg of antibody, incubating the mixture for 4–18 hours at between about 22° C. to 37° C. At the end of the incubation, the mixture is neutralized and purified on a gel-filtration media such as sephadex, sephacryl, biogel, or other suitable media. If Fab fragments are to be used, they are generated by dialyzing the antibodies into phosphate buffer containing 0.1 M cysteine at pH 7.0, adding papain at a similar ratio and incubating the mixture for 18 hours at 37° C. At the end of the incubation period, the mixture is dialyzed to remove excess cysteine and purified on a suitable ion exchange media such as DE-52.

The antibody preparation to be used as the signaling component in the immunoassay is conjugated to a suitable probe for formatting either as a fluorescent assay, an EIA assay, or an RIA. Suitable probes include biotin, FITC, phycoerythrin, alkaline phosphatase, horseradish peroxidase, and B-galactosidase as will be understood by those with skill in the art with reference to the disclosure herein. Because of its flexibility and ability to amplify signals, very often the signaling antibody is conjugated to biotin. The biotinylated antibody permits the use of an enzyme labeled avidin or streptavidin. In a preferred embodiment, horseradish peroxidase conjugated streptavidin is used to reveal biotinylated antibody because it is cheap, stable, easy to use, and generates strong signals with a variety of chromogenic substrates such as ABTS, TMB, OMPD. Antibody is diluted to 10 mg/ml and dialyzed into a high pH buffer (pH=9.5) such as 0.1 M carbonate or 0.1 M borate. Long chain NHS biotin (available from several sources including Pierce, Rockford, Ill.; Sigma Chemical Co.), dissolved in DMF or other suitable solvent and added to the antibody at a molar ratio of approximately 15:1. The mixture is incubated 30–60 minutes and free biotin is removed by dialysis or gel filtration of sephadex G-25, P-10, or other suitable matrix. The conjugated material can be stored at 4° C. with 1% BSA or other carrier protein added as stabilizer. Streptavidin at 10 mg/ml is dialyzed into carbonate buffer at pH 9.5 and HRP also at 10 mg/ml and dialyzed into carbonate buffer at pH 8.0. If the avidin-biotin system is not chosen for use, then antibody can be substituted and conjugated to HRP using identical methods. Sodium periodate is added to the HRP at approximately 1 µg/ml, though this concentration will require optimization according to the lot of HRP. After 2–4 hour at room temperature, periodate is inactivated by the addition of 1/6 w/v or dry G-25 and the streptavidin (or antibody) is added to the mixture. After 18–24 hours, the conjugate is stabilized with sodium borohydride (also 1 µg/ml) and purified by gel-filtration on a matrix such as superose 6 in order to exclude over and under conjugated material.

With respect to information on the Enzyme-linked Immunosorbent Assay (ELISA), serum antibodies and affinity-purified antibodies are tested by direct-binding ELISA. The peptide is coated directly onto 96 well flexible ELISA plates (Costar, Cambridge, Mass.) by passive adsorption at approximately 10 ug/ml in borate-buffered saline (pH 8.2). The plates are then incubated overnight at 4° C., washed with borate-buffered saline containing 0.1% Tween-20®, and blocked for 2 hr at room temperature with 1% bovine serum albumin (BSA) (Boehringer Mannheim) in borate-buffered saline. At this point, the plates can be stored wet in the refrigerator at approximately 4° C. for up to six weeks without significant changes in background and sensitivity. The human sera being tested are added in serial 1:2 dilutions in 1% BSA in borate-buffered saline and incubated overnight at 4° C. Each patient serum is titrated in triplicate through 7 wells from top to bottom of the 96-well plates, leaving the eighth wells empty to serve as a row blank. Following the overnight incubation, the plates are extensively washed with borate-saline-Tween buffer and serum antibodies are then detected using the horseradish peroxidase-conjugated rabbit antibodies described herein. The enzyme-labeled antibodies are diluted 1:5000 in 1% BSA-borate buffer from our 0.5 mg/ml stocks. Each of the triplicate rows of patient serum is developed either with enzyme labeled anti-IgM, anti-IgG, or anti-IgA. After incubation for 3 hr at room temperature, the plates are washed and developed with ABTS substrate (Boehringer Mannheim) in citrate buffer (pH 4.0) and read 10 or 20 minutes later on a semi-automatic plate reader equipped with a 414 nm filter (ICN/Flow Titertek). The backgrounds for each row (the eighth wells) are automatically subtracted from each well of the 7-well titration. Under the assay conditions described, backgrounds on the ELISA plates are small (<0.1 OD).

With respect to the T Cell Assays, proliferative T cell assays are used to measure CMI in patients. Small volume blood samples are layered onto Ficoll-Hypaque and the mononuclear cell-containing interface are collected by pipette. Mononuclear cells collected by lymphoplasmapheresis are used without further processing. Non-adherent cells are harvested, washed, and re-plated in 96 well plates. Cells are plated in triplicate wells at $1 \times 10^6$ cells per ml ($1 \times 10^5$/well) both with and without antigen. Peptides are resuspended in complete culture medium (RPMI and FCS) and added directly to test wells over a wide range of concentrations. After 24–72 hours of culture at 37° C. and 100% humidity, 2 µCi of tritiated thymidine is added. After a further 24 hours of culture, the cells are harvested onto glass fiber filters using a semi-automatic cell harvester. The filters are dried, transferred to scintillation vials and analyzed in an automatic liquid scintillation counter with programmable quench curves and CPM to DPM conversion. The level of T cell proliferation is also proportional to the level of IL-2 production which can be measured in the supernate be monitored using an IL-2 specific ELISA (R&D Systems).

With respect to the diagnostic pathology assays, we use a protocol for the production and long-term storage of glycol methacrylate sections for routine histopathology and histocytochemistry. Sections obtained by this protocol allow immunolabelling for many different antigens and standard histological staining can also be performed on these sections. Multiple labeling of consecutive thin sections or potentially on the same section can be performed while preserving structural organization. We combine freeze-substitution with low temperature plastic embedding. Fresh tissue is obtained and immediately frozen in melting isopentane precooled in liquid nitrogen. Tissue samples should have the maximum dimensions of 1.0×0.5×0.2 cm. They are then placed in acetone for 48 hours at −20° C. to −30° C., then in glycol methacrylate resin for 24 hours at −20° C. to −30° C., and then in glycol methacrylate resin under a vacuum for 2 hours at −20° C. to −30° C. The specimen is placed in a mold with glycol methacrylate resin plus catalyst for polymerization, under a vacuum overnight at −20° C. to −30° C. The blocks are brought to room temperature and sectioned with glass or tungsten-carbide knives. We prefer to use horseradish peroxidase conjugates for immunostaining. The substrate we employ is DAB with $CuSO_4$ amplification. This gives us good results and is compatible with a hematoxylin counterstain. The resulting slides can be permanently mounted, are easily analyzed by light microscopy, and are compatible with quantitative image analysis using automatic scanning equipment.

X. DIAGNOSTIC KIT FOR DETECTING THE PRESENCE OF ANTIBODY IN SAMPLES

According to another aspect of the present invention, there is provided a diagnostic kit for detecting the presence of antibody in the samples including serum samples taken from normal donors, patients suspected of having disease, and patients with diseases who are being monitored throughout the course of treatment or remission. Levels of antibody detected by the immunoassay which are significantly higher than the baseline levels of a statistically significant population size of known normal donors without evidence of active disease are considered to be indicative of active disease.

The kit, according to the present invention, can include the following:
1) 96 well high binding Elisa plates (Costar)
2) Peptide dissolved in sodium carbonate buffer (approximately pH 9.0)
3) 1% Bovine serum albumin in borate or carbonate buffer (Sigma Chemical Co.)
4) HRP substrate ABTS® (2,2'-azino-di-(3-ethyl-benzthiazoline-sulfonic acid)
5) 30% hydrogen peroxide (Boehringer Mannheim)
6) Biotinylated rabbit anti-human IgM
7) Biotinylated rabbit anti-human IgG
8) Biotinylated rabbit anti-human IgA
9) Standardized high titer human serum
10) Standardized low titer human serum
11) Streptavidin conjugated to horseradish peroxidase In a preferred embodiment, the kit includes one or more of the following:
12) Wet-boxes
13) Adjustable automatic pipettors, multi-channel pipetor, disposable pipette tips
14) Solution/Substrate reservoirs
15) Azide free 50–100 mM citric acid in distilled water, pH adjusted to approximately 4.0
16) Borate buffered saline pH adjusted to approximately 8.5

XI. METHOD OF USING DIAGNOSTIC KIT FOR DETECTING THE PRESENCE OF ANTIBODY IN SAMPLES

According to another embodiment of the present invention, there is provided a method of using the diagnostic kit disclosed herein, comprising the following steps:

1) Coat each well of the ELISA plate(s) with 100 µl of peptide solution. Place the plate(s) in a wetbox and incubate overnight at 4° C.
2) Empty the plate(s) and wash them 2–3 times with carbonate or borate buffer. Block unreacted sites on the plates by flooding or completely filling the plate wells with the 1% BSA solution for at least about 1 hr at room temperature.
3) Empty and wash the plates 2–3 times and add 50–100 µl of test material Serum or CSF to the wells. Titrate in dilutions of 1:2. Incubate the plates 3–4 hours at room temperature or overnight at 4° C.
4) Empty and wash the plates 3–4 times and add to each well 100 µl HRP-labeled secondary antibody in 1% BSA. Incubate the plates 3–4 hours at room temperature or overnight at 4° C.
5) Empty and wash the plates 3–4 times; empty completely and add to each well 100 µl of freshly prepared substrate; dissolve 15 mg ABTS in 1 ml of glass distilled water (if stored in the dark this solution is stable for several weeks). To 10 ml of citrate buffer add 0.2 ml of the ABTS solution and 10 µl of 30% $H_2O_2$.
6) Incubate the plate at room temperature. A blue-green reaction product will form in the positive wells. The plate can be read at a wavelength of 405 nm or 414 mm in a standard ELISA plate reader. If desired, the color development can be stopped by addition to the wells of 10 µl of 0.1% sodium azide.

The majority of auto-antibody tests are semi-quantitative and results are reported in arbitrary or standardized international units. A few tests incorporate a standardized serum sample for which a true specific antibody concentration has been determined in milligrams per milliliter or deciliter which allows a more precise concentration to be reported. In some cases, it may be possible to generate an antigen independent titration curve based on purified human myeloma proteins which can also be used to generate true specific antibody concentrations.

Once significant amounts of data have been generated, a statistical analysis will yield specific cutoff points which will be used to establish the sensitivity and specificity of the test. These calculations are used not only to validate the test but also used to help determine the accuracy of an individual diagnosis based on the result of the test.

In some cases, antibody concentration is calculated as an antibody index according to the following formula $$(\text{Specific IgG in CSF/Total IgG in CSF})/(\text{Specific IgG in Serum/Total IgG in Serum}) \qquad \text{EQ.1}$$

EXAMPLE I

A METHOD OF DIAGNOSING DISEASE BY DETECTING ANTIBODY IN A SAMPLE

According to one aspect of the present invention, there is provided a method of diagnosing disease in a human or animal. The method involves the steps of, first, determining an epitope of a peptide, protein, or protein homologue to which antibodies are produced in the disease or condition, by (a) providing a sample of tissue or fluid from one or more patients, wherein the sample contains antibodies directed toward a peptide, protein, or protein homologue having the epitope; (b) providing a device for identifying an epitope region of a peptide, protein, or protein homologue, the device comprising a support having a plurality of sequentially oriented peptide spots, each spot containing a peptide having an amino acid sequence. The peptide, protein, or protein homologue to which antibody production is directed has a known amino acid sequence, and the amino acid sequence of the peptides contained on the peptide spots sequentially progress through the amino acid sequence of the peptide, protein, or protein homologue to which antibody production is directed. Then, (c) at least part of the sample is applied to the device, thereby determining the immunoreactivity of the sample to a peptide on one or more peptide spots. Immunoreactivity of the sample indicates the presence of at least part of the epitope within the peptide sequence contained on the spot. In a preferred embodiment, the support is a polypropylene membrane. In another preferred embodiment, the sample is selected from the group consisting of cerebral spinal fluid, blood, tears and saliva.

After determining an epitope to which antibody production is directed against a peptide, protein, or protein homologue, a sample of tissue or fluid from a patient which potentially contains antibodies which are characteristic of the disease or condition is provided. Then, the immunoreactivity of the sample to a peptide or protein having the epitope determined in the first step is determined. The determined immunoreactivity is compared to an immunoreactivity of one or more subjects known to have the disease or condition or one or more subjects known not to have the disease or condition. An immunoreactivity of the patient sample above the range of the subject or subjects known not to have the disease or condition, or an immunoreactivity of the patient sample in the range of the subject or subject known to have the disease or condition indicates that the patient has the disease or condition.

In a preferred embodiment, the disease or condition is an autoimmune disease. Examples of autoimmune diseases arthritis, diabetes, Grave's disease, Hashimoto's, multiple sclerosis, myasthenia gravis, scleroderma and systemic lupus erythematous.

EXAMPLE II

A METHOD OF DIAGNOSING DISEASE BY DETECTING EXPRESSION OF OSP

According to another aspect of the present invention, there is provided another method of diagnosing disease in a human or animal. The method involves the steps of, first, detecting expression of OSP in a biological sample, such as cerebral spinal fluid, blood, tears, saliva or a biopsy specimen. Next, the amount of OSP in the sample is compared to the amount of OSP expected for a normal sample or a sample of known pathology. Then, a diagnosis is made based, at least in part, on the comparison. In one embodiment, the disease is human meningioma and the sample is a biopsy of a human meningioma.

EXAMPLE III

DETERMINATION OF "OLIGODENDROCYTE-SPECIFIC PROTEIN PEPTIDE," THE IMMUNOREACTIVE REGION OLIGODENDROCYTE-SPECIFIC PROTEIN AND OTHER IMMUNOREACTIVE SEQUENCES

Using the device comprising a polypropylene membrane disclosed herein, we determined the immunoreactive region of oligodendrocyte-specific protein as follows. Oligodendrocyte-specific protein was calculated as ninety-six (96) overlapping ten residue peptides using a computer program. While various computer programs can be constructed to perform these calculations, one such computer program is given in Appendix I (coded in "Foxpro", (Microsoft Corp. Seattle, Wash.) database language utilizing a "Foxpro" database) given in Appendix II. The computer program can be coded in other programming languages utilizing other database systems, as will be understood by those with skill in the art with reference to the disclosure herein. The computer program can be run on a personal computer or any general purpose system. The text file expressed oligodendrocyte-specific protein, SEQ ID NO:2, as sequential amino acids from a one letter code. Appendix II lists the 96 peptide sequences generated by the program and text file. The program accepts direction of text, number of peptides and number of residues per peptide parameters as user input. Preferably, the program runs on a Windows operating system.

Once the appropriate peptide sequences were determined, these peptides were synthesized on a device comprising a polypropylene membrane, according to the disclosure herein, which comprised an insoluble support including a polypropylene membrane as disclosed herein having 96 spots. After synthesis, each spot contained one peptide sequence where the amino acid sequence of the peptide sequences sequentially progress through the amino acid sequence of oligodendrocyte-specific protein.

Once the device to determine the immunoreactive regions of oligodendrocyte-specific protein was constructed, the membrane was wetted in borate-buffered saline, pH 7.5–8.5, containing 0.05% Tween-20®. Then, the membrane was blocked in blocking buffer containing 1% BSA and incubation for 1–2 hours in a volume that completely immersed the membrane. Next, the membrane was washed 5–7 times in borate buffer.

CSF pooled from five (5), 1 ml samples taken from five patients with multiple sclerosis were used as a source of primary antibodies. This pooled sample was diluted in 50 ml of borate buffer. The membrane was incubated by shaking in this solution overnight. The membrane was then washed 5–7 time in borate buffer.

Biotin-labeled secondary antibody was diluted 1:1000 in borate buffer. The membrane was incubated in this solution for 2 hours and then washed 5–7 times in borate buffer.

Next the membrane was incubated with streptavidin-alkaline phosphatase conjugate diluted 1:1000 in borate buffer for 2 hours and then washed 5–7 times in borate buffer.

The membrane was then transferred to a new container containing substrate Nitroblue tetrazolium and Bromo-chloroindolyl-phosphate (NBT/BCIP) solution made according to the manufacturer's instructions and incubated until spots were clearly visible. Then, the membrane was removed and dried before background staining levels were high.

The most consistently positive reaction showed for the peptide corresponding to spot 58 in Appendix III. This peptide was named "oligodendrocyte-specific protein peptide",which had the following amino acid sequence: Ala-Lys-Tyr-Arg-Arg-Ala-Gln-Leu-Ala-Gly, residues 115–124 of SEQ ID NO:2. Several other peptide sequences were also found to be immunoreactive though less consistently immunoreactive. They are as follows: Thr-Ser-Thr-Asn-Asp-Trp-Val-Val-Thr-Cys-Ser-Tyr-Thr-Ile-Pro-Thr, residues 25–40 of SEQ ID NO:2; Gly-Leu-Tyr-His-Cys-Lys-Pro-Leu-Val-Asp-Ile-Leu, residues 61–72 of SEQ ID NO:2; Phe-Pro-Val-Cys-Ala-His-Arg-Glu-Ile-Thr-Ile-Val-Ser-Phe, residues 141–154 of SEQ ID NO:2; Gly-Tyr-Ser- Leu-Tyr-Ala-Gly-Trp-Ile-Gly-Ala-Val-Met-Cys-Leu-Val, residues 161–170 of SEQ ID NO:2; Tyr-Val-Gln-Ala-Cys-Arg-Ala-Leu-Met-Ile-Ala-Ala, residues 77–88 of SEQ ID NO:2.

Therefore, according to another aspect of the present invention, there is provided a purified and isolated peptide having the sequence Ala-Lys-Tyr-Arg-Arg-Ala-Gln-Leu-Ala-Gly, residues 115–124 of SEQ ID NO:2. There is also provided a recombinant peptide having this sequence, and a peptide recognized by a monoclonal antibody having affinity to this peptide.

Further, there is provided a high affinity monoclonal antibody which immunoreacts with this peptide, the monoclonal antibody made according to techniques understood by those with skill in the art with reference to the disclosure herein. The antibody can have an Fc portion selected from the group consisting of the IgM class, the IgG class and the IgA class.

EXAMPLE IV

DETERMINATION OF ANTIGENIC RESPONSE TO OLIGODENDROCYTE-SPECIFIC PROTEIN PEPTIDE IN MULTIPLE SCLEROSIS

In order to determine if oligodendrocyte-specific protein was an antigen in an immune mediated demyelinating disease such as various forms of multiple sclerosis, we performed Western blot analysis and enzyme-linked immunoabsorbent assay (ELISA) of samples of cerebral spinal fluid of patients with multiple sclerosis, patients with other diseases of the central nervous system and normal controls as follows.

First, we tested eight samples of cerebral spinal fluid for antibodies against oligodendrocyte-specific protein using human brain homogenate and recombinant mouse oligodendrocyte-specific protein as antigens to perform Western blot analysis. Six of the cerebral spinal fluid samples were obtained from patients with the relapsing remitting form of multiple sclerosis through the UCLA School of Medicine. The remaining two normal control samples were obtained from the National Neurological Research Specimen Bank. All six of the samples from patients with relapsing remitting multiple sclerosis demonstrated antibodies to recombinant mouse oligodendrocyte-specific fusion protein (26 kDa). The samples also demonstrated antibodies to a protein in the human brain homogenate which appeared to be human oligodendrocyte-specific protein by molecular weight (22 kDa). Further, the mouse anti-OSP polyclonal antibodies reacted against identical bands in Western blots containing human brain homogenates and recombinant oligodendrocyte-specific protein.

Based on these preliminary results, we developed a semi-quantitative and rapid method of determining the levels of anti-OSP antibodies in a large number of samples using synthetic peptides and the methods disclosed herein. Briefly, a total of 96 overlapping peptides spanning the entire murine 207 amino acid protein, SEQ ID NO:2, were synthesized and bound to a solid phase polypropylene membrane according to the methods disclosed herein. Each peptide was incubated to determine the presence of antibodies against specific sequences of the oligodendrocyte-specific protein. Several antigenic regions were found. The strongest antigenic region was a 10 (ten) amino acid peptide sequence having the sequence Ala-Lys-Tyr-Arg-Arg-Ala-Gln-Leu-Ala-Gly, residues 115–124 of SEQ ID NO:2.

Using this antigenic peptide, residues 115–124 of SEQ ID NO:2, we tested the samples of cerebral spinal fluid of patients with multiple sclerosis, patients with other diseases of the central nervous system and normal controls as follows using enzyme-linked immunoabsorbent assay (ELISA). In a first study, twenty-four (24) of thirty (30), that is eighty percent (80%), of CSF samples from patients with relapsing remitting (RR) multiple sclerosis (stable for at least one month) had an ELISA optical density units greater than 0.55 (mean±SD, 0.74±0.35). Two (2) of the ten (10), that is twenty percent (20%), of CSF samples from patients with chronic progressive (CP) multiple sclerosis had an ELISA optical density units greater than 0.55 (0.39±0.32). None of the eight (8) CSF samples from patients with HTLV-1 associated myelopathy (HAM) (an inflammatory disease of myelin) patients (0.29±0.17) and none of the nine (9) normal controls (0.33±0.09) had an ELISA optical density units greater than 0.55. No antibody reaction was observed using the other overlapping peptides of oligodendrocyte-specific protein.

In a second study, twenty-four (24) of forty-eight (48), that is fifty percent (50%), of CSF samples from patients with relapsing remitting (RR) multiple sclerosis had an ELISA optical density units greater than 0.55 (mean, 0.58). Three (3) of the fifty-four (54), that is six percent (6%), of CSF samples from patients with chronic progressive (CONTINUATION-IN-PART) multiple sclerosis had an ELISA optical density units greater than 0.55 (mean, 0.34). Six (6) of the forty (40), that is fifteen percent (15%), of the controls (patients having meningitis, encephalitis, stroke and other diseases) had an ELISA optical density units greater than 0.55.

There were no differences in antibody levels directed against oligodendrocyte-specific protein in blood from all groups tested, that is both controls and multiple sclerosis patients nor were there antibodies in spinal fluid from any of the groups which reacted against the other overlapping peptides of oligodendrocyte-specific protein tested.

The data from these studies demonstrate that anti-OSP antibodies are present in significant titers in CSF of the majority of patients with relapsing remitting multiple sclerosis. The differences in antibody levels between patients in the two studies could be due to several factors. First, the stability of antibodies is affected by the age of the sample and the method of storage. CSF samples in the second study were older and some samples were heat sealed. In addition, the patients as a group were significantly older and were all males. Therefore, these samples were less likely to react. Further, the diagnostic criteria used to categorize patients into types of multiple sclerosis could have been different between the two studies due to the different sources of samples.

The oligodendrocyte-specific protein peptide, residues 115–124 of SEQ ID NO:2, has significant homology with several viral and bacterial proteins from such species as HSV, EBV and *E. coli*, and many of the substitutions are between similar amino acids. This homology suggests the possibility that an immune response directed against a pathogen may also react with a common antigenic epitope of oligodendrocyte-specific protein leading to the demyelination found in multiple sclerosis.

Therefore, according to another aspect of the present invention, there is provided a method of diagnosis multiple sclerosis comprising the steps of, first, providing a sample of tissue or fluid from a patient; second, determining immunoreactivity of the sample to a peptide having the sequence Ala-Lys-Tyr-Arg-Arg-Ala-Gln-Leu-Ala-Gly, residues 115–124 of SEQ ID NO:2 or to oligodendrocyte-specific protein; and comparing the determined immunoreactivity to an immunoreactivity of one or more subjects known to have multiple sclerosis or one or more subjects known not to have multiple sclerosis, where an immunoreactivity of the patient sample above the range of the normal subject or subjects, or an immunoreactivity of the patient sample in the range of the subject or subject known to have multiple sclerosis indicates that the patient has multiple sclerosis. The tissue or fluid sample can be cerebral spinal fluid, blood, tears or saliva, among other appropriate samples.

EXAMPLE V

DETERMINATION OF OSP EXPRESSION IN HUMAN MENINGIOMAS

Human OSP expression was measured using Northern blot analysis in developing mouse meninges, adult meninges, human meningiomas and human glioblastomas and compared to normal human brain controls from autopsy and surgical specimens. OSP expression was significantly higher in 5 of 5 meningiomas but was lower in 8 of 9 glioblastomas, suggesting that OSP acts as a proto-oncogene. Further, in situ hybridization demonstrated high levels of OSP expression in developing mouse meninges but not in adult mouse meninges. These data suggest that OSP plays an important role in growth regulation and development.

EXAMPLE VI

METHOD OF DIAGNOSING OR TREATING DISEASE

According to another aspect of the present invention, there is provided a method of treating disease in a human or animal. The method involves the steps of, first, diagnosing a condition or disease as disclosed herein, such as in Example I or Example II, and then treating the patient found to have the condition or disease.

For example, in order to treat a patient with remitting relapsing multiple sclerosis, a sample of the patient's CSF is provided. Next, immunoreactivity of the sample to oligodendrocyte-specific protein peptide, residues 115–124 of SEQ ID NO:2 is determined according to the disclosure herein. If the patient's CSF sample is found to contain antibodies to oligodendrocyte-specific protein peptide, residues 115–124 of SEQ ID NO:2 as indicated by the methods disclosed herein, the patient is given a provisional diagnosis of relapsing remitting multiple sclerosis and treatment, such as the administration of steroid, is initiated. Other diseases suitable for treatment by this method include some forms of arthritis, diabetes, Grave's disease, Hashimoto's, multiple sclerosis, myasthenia gravis, scleroderma and systemic lupus erythematous.

Alternately, a biopsy sample of a human brain tumor is taken and the amount of OSP expressed in the sample is determined and compared with known amounts from normal tissue and various brain tumors. Once a diagnosis of meningioma is made based on the comparison, a treatment regimen, such as surgical resection is undertaken.

Although the present invention has been described with reference to certain preferred embodiments, many other embodiments will be apparent to those with skill in the art. For example, the device, kit and methods according to the present invention can by used to map epitope specificity of monoclonal and polyclonal antibodies, to select relevant peptides for immunogen selection and vaccine development, to predict relevant peptides for production of "monospecific polyclonal" antibodies and to generate small scale—rapidly definable combinatorial peptide libraries. Therefore, the spirit and scope of the appended claims should not be limited to the description of the preferred versions contained herein.

APPENDIX I

® Robert Seitz 1995

```
@0,0 CLEAR
CLOSE ALL
GETFILE = SPACE(8)
EXITFILE = SPACE(8)
@1,1 SAY "ENTER THE TEXT FILE YOU WISH TO SUBDIVIDE";
    GET GETFILE PICTURE '!!!!!!!!'
@2,1 SAY "ENTER THE 96 PEPTIDE TEXT FILE";
    GET EXITFILE PICTURE '!!!!!!!!'
READ
GETFILE = 'I: \ANTIBODI\ '+ALLTRIM(GETFILE)+'.TXT'
EXITFILE = 'I: \ANTIBODI\ '+ALLTRIM(EXITFILE)+'.TXT'
MPROTEIN = FOPEN(getfile,0)
PROSIZE = FSEEK(MPROTEIN,0,2)
PROSTART = FSEEK(MPROTEIN,0)
@0,0 CLEAR
PEP = fread(mprotein,prosize)
SIZE = 96 &&48
LENGTH = 10
@1,1 SAY "How many peptides?" GET size
@2,1 SAY "What length peptide?" GET length
READ
COUNT = prosize
DIVISOR = COUNT/SIZE
WHOLE = FLOOR(DIVISOR)
FRAG = DIVISOR-WHOLE
COUNTER = 0
POS = 1
CREATE CURSOR temp (PEPTIDE C(30), overlap N(2,0),pep_num N(2.0))
start = 1
new_size = size &&-1
FOR start = 1 TO new_size
    APPEND BLANK
    mpep = SUBSTR(pep,pos,length)
    counter = counter + frag
    adjuster1 = FLOOR(counter)
    adjuster2 = whole + adjuster1
    counter = counter-adjuster1
    pos = pos + adjuster2
    common = 10-adjuster2
    REPLACE peptide WITH UPPER(mpep),;
        overlap WITH COMMON,;
        pep_num WITH recno( )
ENDFOR
GO new_size
pos = count-length + 1
mpep = SUBSTR(pep,pos)
WAIT
COPY TO &exitfile FIELDS peptide TYPE DELIMITED WITH BLANK
CLOSE ALL
RETURN
*BROW
```

APPENDIX III

1. MVATCLQVVG, residues 1–10 of SEQ ID NO:2
2. ATCLQVVGQV, residues 3–12 of SEQ ID NO:2
3. CLQVVGQVVG, residues 5–14 of SEQ ID NO:2
4. QVVGEVTSFV, residues 7–16 of SEQ ID NO:2
5. VGEVTSFVTS, residues 9–18 of SEQ ID NO:2
6. EVTSFVTSFV, residues 11–20 of SEQ ID NO:2
7. TSFVGWIGII, residues 13–22 of SEQ ID NO:2
8. FVGWIGIIVT, residues 15–24 of SEQ ID NO:2
9. GWIGIIVTTS, residues 17–26 of SEQ ID NO:2
10. IGIIVTTSTN, residues 19–28 of SEQ ID NO:2
11. IIVTTSTNDW, residues 21–30 of SEQ ID NO:2
12. VTTSTNDWVV, residues 23–32 of SEQ ID NO:2
13. TSTNDWVVTC, residues 25–34 of SEQ ID NO:2

APPENDIX III-continued

14. TNDWVVTCSY, residues 27–36 of SEQ ID NO:2
15. DWVVTCSYTI, residues 29–38 of SEQ ID NO:2
16. VVTCSYTIPT, residues 31–40 of SEQ ID NO:2
17. TCSYTIPTCR, residues 33–42 of SEQ ID NO:2
18. SYTIPTCRKM, residues 35–44 of SEQ ID NO:2
19. TIPTCRKMDE, residues 37–46 of SEQ ID NO:2
20. PTCRKMDEKM, residues 39–48 of SEQ ID NO:2
21. CRKMDEKMDE, residues 41–50 of SEQ ID NO:2
22. KMDELGSKGL, residues 43–52 of SEQ ID NO:2
23. DELGSKGLWA, residues 45–54 of SEQ ID NO:2
24. LGSKGLWADC, residues 47–56 of SEQ ID NO:2
25. SKGLWADCVM, residues 49–58 of SEQ ID NO:2
26. GLWADCVMAT, residues 51–60 of SEQ ID NO:2
27. WADCVMATGL, residues 53–62 of SEQ ID NO:2
28. DCVMATGLYH, residues 55–64 of SEQ ID NO:2
29. VMATGLYHCK, residues 57–66 of SEQ ID NO:2
30. ATGLYHCKPL, residues 59–68 of SEQ ID NO:2
31. GLYHCKPLVD, residues 61–70 of SEQ ID NO:2
32. YHCKPLVDIL, residues 63–72 of SEQ ID NO:2
33. CKPLVDILIL, residues 65–74 of SEQ ID NO:2
34. PLVDILILPG, residues 67–76 of SEQ ID NO:2
35. VDILILPGYV, residues 69–78 of SEQ ID NO:2
36. ILILPGYVQA, residues 71–80 of SEQ ID NO:2
37. ILPGYVQACR, residues 73–82 of SEQ ID NO:2
38. PGYVQACRAL, residues 75–84 of SEQ ID NO:2
39. YVQACRALMI, residues 77–86 of SEQ ID NO:2
40. QACRALMIAA, residues 79–88 of SEQ ID NO:2
41. CRALMIAASV, residues 81–90 of SEQ ID NO:2
42. ALMIAASVLG, residues 83–92 of SEQ ID NO:2
43. MIAASVLGLP, residues 85–94 of SEQ ID NO:2
44. AASVLGLPAI, residues 87–96 of SEQ ID NO:2
45. SVLGLPAILL, residues 89–98 of SEQ ID NO:2
46. LGLPAILLLL, residues 91–100 of SEQ ID NO:2
47. LPAILLLLTV, residues 93–102 of SEQ ID NO:2
48. AILLLLTVLP, residues 95–104 of SEQ ID NO:2
49. LLLLTVLPCI, residues 97–106 of SEQ ID NO:2
50. LLTVLPCIRM, residues 99–108 of SEQ ID NO:2
51. TVLPCIRMGH, residues 101–110 of SEQ ID NO:2
52. LPCIRMGHEP, residues 103–112 of SEQ ID NO:2
53. CIRMGHEPGV, residues 105–114 of SEQ ID NO:2
54. RMGHEPGVAK, residues 107–116 of SEQ ID NO:2
55. GHEPGVAKYR, residues 109–118 of SEQ ID NO:2
56. EPGVAKYRRA, residues 111–120 of SEQ ID NO:2
57. GVAKYRRAQL, residues 113–122 of SEQ ID NO:2
58. AKYRRAQLAG, residues 115–124 of SEQ ID NO:2
59. YRRAQLAGVL, residues 117–126 of SEQ ID NO:2
60. RAQLAGVLLI, residues 119–128 of SEQ ID NO:2
61. QLAGVLLILL, residues 121–130 of SEQ ID NO:2
62. GVLLILLALC, residues 124–133 of SEQ ID NO:2
63. LILLALCAIV, residues 127–136 of SEQ ID NO:2
64. LLALCAIVAT, residues 129–138 of SEQ ID NO:2
65. ALCAIVATIW, residues 131–140 of SEQ ID NO:2
66. CAIVATIWFP, residues 133–142 of SEQ ID NO:2
67. IVATIWFPVC, residues 135–144 of SEQ ID NO:2
68. ATIWFPVCAH1 residues 137–146 of SEQ ID NO:2
69. IWFPVCAHRE, residues 139–148 of SEQ ID NO:2
70. FPVCAHREIT, residues 141–150 of SEQ ID NO:2
71. VCAHREITIV, residues 143–152 of SEQ ID NO:2
72. AHREITIVSF, residues 145–154 of SEQ ID NO:2
73. REITIVSFGY, residues 147–156 of SEQ ID NO:2
74. ITIVSFGYSL, residues 149–158 of SEQ ID NO:2
75. IVSFGYSLYA, residues 151–160 of SEQ ID NO:2
76. SFGYSLYAGW, residues 153–162 of SEQ ID NO:2
77. GYSLYAGWIG, residues 155–164 of SEQ ID NO:2
78. SLYAGWIGAV, residues 157–166 of SEQ ID NO:2
79. YAGWIGAVMC, residues 159–168 of SEQ ID NO:2
80. GWIGAVMCLV, residues 161–170 of SEQ ID NO:2
81. IGAVMCLVGG, residues 163–172 of SEQ ID NO:2
82. AVMCLVGGCV, residues 165–174 of SEQ ID NO:2
83. MCLVGGCVIV, residues 167–176 of SEQ ID NO:2
84. LVGGCVIVCC, residues 169–178 of SEQ ID NO:2
85. GGCVIVCCSG, residues 171–180 of SEQ ID NO:2
86. CVIVCCSGDA, residues 173–182 of SEQ ID NO:2
87. IVCCSGDAQS, residues 175–184 of SEQ ID NO:2
88. CCSGDAQSFG, residues 177–186 of SEQ ID NO:2
89. SGDAQSFGEN, residues 179–188 of SEQ ID NO:2
90. DAQSFGENRF, residues 181–190 of SEQ ID NO:2
91. QSFGENRFYY, residues 183–192 of SEQ ID NO:2
92. FGENRFYYSS, residues 185–194 of SEQ ID NO:2
93. ENRFYYSSGS, residues 187–196 of SEQ ID NO:2
94. SSGSSSPTHA, residues 193–202 of SEQ ID NO:2
95. GSSSPTHAKS, residues 195–204 of SEQ ID NO:2
96. SPTHAKSAHV, residues 198–207 of SEQ ID NO:2

What is claimed is:

1. An isolated DNA segment comprising SEQ ID NO: 1.
2. An isolated DNA segment fully complementary to the DNA segment of claim 1.
3. An isolated DNA segment consisting essentially of a nucleotide sequence according to SEQ ID NO: 1.
4. An isolated DNA segment fully complementary to the DNA segment of claim 3.
5. A vector containing the DNA segment of claim 1.
6. A vector containing the DNA segment of claim 2.
7. An isolated prokaryotic or eukaryotic host cell stably transformed or transfected by the vector of claim 5.
8. An isolated prokaryotic or eukaryotic host cell stably transformed or transfected by the vector of claim 6.
9. A method of making a protein, comprising the steps of:
 (a) culturing a microorganism transformed with the DNA segment according to claim 1; and
 (b) recovering the protein encoded by the DNA segment.

* * * * *